United States Patent
Ishiguro et al.

(10) Patent No.: US 6,867,297 B1
(45) Date of Patent: Mar. 15, 2005

(54) PROCESS FOR SYNTHESIZING 4-SUBSTITUTED AZETIDINONE DERIVATIVES

(75) Inventors: Masaji Ishiguro, Takarazuka (JP); Takashi Nakatsuka, Mishima (JP); Rie Tanaka, Ibaraki (JP); Tetsuo Shimamoto, Suita (JP); Takuro Yoshida, Tatebayashi (JP)

(73) Assignee: Daiichi Suntory Pharma Co., Ltd., Tokyo (JP)

( * ) Notice: Subject to any disclaimer, the term of this patent is extended or adjusted under 35 U.S.C. 154(b) by 40 days.

(21) Appl. No.: 09/178,594

(22) Filed: Oct. 26, 1998

Related U.S. Application Data

(63) Continuation of application No. 08/797,851, filed on Feb. 10, 1997, now abandoned, which is a continuation of application No. 08/318,686, filed as application No. PCT/JP94/00195 on Feb. 10, 1994, now abandoned.

(30) Foreign Application Priority Data

Feb. 12, 1993 (JP) .............................................. 5-47552

(51) Int. Cl.$^7$ ......................................... C07D 205/08
(52) U.S. Cl. ..................................................... 540/200
(58) Field of Search ........................................ 540/200

(56) References Cited

U.S. PATENT DOCUMENTS 5,026,844 A * 6/1991 Ishiguro
6,011,150 A * 1/2000 Iwasaki et al. ............. 540/200

OTHER PUBLICATIONS

Reetz, Tet Letters 1455, 1978.*

* cited by examiner

Primary Examiner—Mark L. Berch
(74) Attorney, Agent, or Firm—Jacobson Holman PLLC

(57) ABSTRACT

An azetidinone derivative represented by the general formula (1)

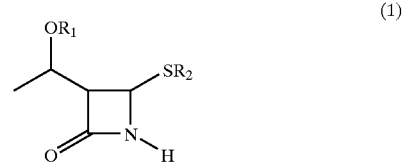

(1)

(wherein $OR_1$ is a protected hydroxyl group; $R_2$ is a substituted or unsubstituted alkyl group, a substituted or unsubstituted alkenyl group or a substituted or unsubstituted aromatic group) is reacted with an ester compound represented by the formula (2)

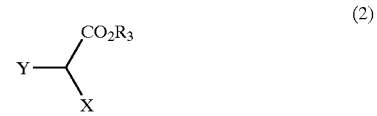

(2)

(wherein $CO_2R_3$ is an esterified carboxyl group; X and Y are the same or different and represent individually a substituted or unsubstituted alkyl group, a substituted or unsubstituted alkenyl group, a substituted or unsubstituted aralkyl group, a substituted or unsubstituted aryl group, a substituted or unsubstituted alkylthio group, a substituted or unsubstituted alkenylthio group, a substituted or unsubstituted aralkylthio group, a substituted or unsubstituted arylthio group, a substituted or unsubstituted alkyloxy group, a substituted or unsubstituted alkenyloxy group, a substituted or unsubstituted aralkyloxy group, a substituted or unsubstituted aryloxy group, a substituted or unsubstituted silyloxy group, a substituted or unsubstituted heterocyclic group, a substituted or unsubstituted heterocyclic-thio group, a substituted or unsubstituted heterocyclic-oxy group, a substituted or unsubstituted acyl group, a substituted or unsubstituted ester group, a substituted or unsubstituted thio ester group, a substituted or unsubstituted amide group, a substituted or unsubstituted amino group, a hydrogen atom or halogen atom, or are taken together with each other to form a substituted or unsubstituted cycloalkan-2-on-1-yl group) in the presence of zinc and copper compounds to synthesis a 4-substituted azetidinone derivative represented by the formula (3)

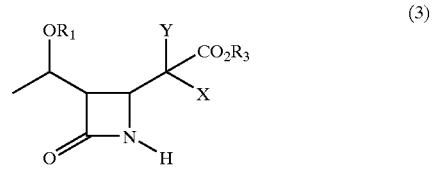

(3)

(wherein $OR_1$, $CO_2R_3$, X and Y are as defined above).

5 Claims, No Drawings

PROCESS FOR SYNTHESIZING 4-SUBSTITUTED AZETIDINONE DERIVATIVES

This application is a CON of Ser. No. 08/797,851, filed Feb. 10, 1997, ABN, which is a CON of Ser. No. 08/318,686, filed Oct. 11, 1994, ABN, which is a 371 of PCT/JP94/00195, filed Feb. 10, 1994.

TECHNICAL FIELD

The present invention relates to a process for producing 4-substituted azetidinone derivatives which are important as a synthetic intermediate for carbapenem based antimicrobial agents and the like.

BACKGROUND ART

There have already been reported several useful processes (for example, Japanese Unexamined Patent Publication No. 61-207373) for producing azetidinone derivatives represented by the general formula (1)

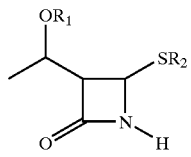

(1)

(wherein $OR_1$ is a protected hydroxyl group; $R_2$ is a substituted or unsubstituted alkyl group, a substituted or unsubstituted alkenyl group or a substituted or substituted aromatic group). In making an attempt to produce from such azetidinone derivatives of the general formula (1) substituted azetidinone derivatives represented by the general formula [3]:

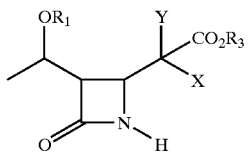

(3)

(wherein $OR_1$ is as defined above; $CO_2R_3$ is an esterified carboxyl group; X and Y are the same or different and represent individually a substituted or unsubstituted alkyl group, a substituted or unsubstituted alkenyl group, a substituted or unsubstituted aralkyl group, a substituted or unsubstituted aryl group, a substituted or unsubstituted alkylthio group, a substituted or unsubstituted alkenylthio group, a substituted or unsubstituted aralkylthio group, a substituted or unsubstituted arylthio group, a substituted or unsubstituted alkyloxy group, a substituted or unsubstituted alkenyloxy group, a substituted or unsubstituted aralkyloxy group, a substituted or unsubstituted aryloxy group, a substituted or unsubstituted silyloxy group, a substituted or unsubstituted heterocyclic group, a substituted or unsubstituted heterocyclic-thio group, a substituted or unsubstituted heterocyclic-thio group, a substituted or unsubstituted acyl group, a substituted or unsubstituted ester group, a substituted or unsubstituted thioester group, a substituted or unsubstituted amide group, substituted or unsubstituted amino group, a hydrogen atom or a halogen atom, or are taken together with each other to form a substituted or unsubstituted cycloalkan-2-on-1-yl group), it has been necessary to oxidize the sulfide group of the azetidinone derivative of the general formula (1) to thereby convert the group to the more readily removable sulfone group or to substitute the acyloxy group for the sulfide group.

In order to convert the azetidinone derivative of the general formula [1] to the corresponding sulfone-containing derivative, there is known a method utilizing peroxy acid (Yoshida et al., Chem. Pharm. Bull, 29, 2899 (1981)), while a method using a mercury compound (Yoshida et al., Chem. Pharm. Bull., 29, 2899 (1981)) is known for the conversion of the same to the acyloxy-containing derivative, but difficulties are encountered in bringing these methods into commercial practice in terms of hygiene, safety or toxicity and the like.

Referring to the conversion of (1) to the acyloxy derivative, there has recently been reported a useful method involving the use of a copper compound (Japanese Unexamined Patent Publication No. 3-163057), resulting in marked improvement in the commercial production of the said derivative. Nevertheless, this method requires heating in carrying out the reaction and is yet to be improved. On the other hand, there have been reported a method (Japanese Unexamined Patent Publication No. 3-157365) of directly converting the azetidinone derivative of the general formula [1] to the azetidinone derivative of the general formula [3]:

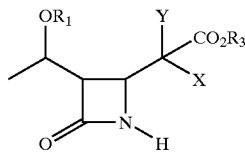

(3)

(wherein $OR_1$, $CO_2R_3$, X and Y are as defined above) and also a method (Ito et al., Tetrahedron, 47, 2801 (1991)) of converting an acryloxyacetidinone derivative to an azetidinone derivative of the general formula [3], which methods have been developed with a specific view to introducing a substituent into the 1-methylene group to enhance the chemical and in vivo stabilities of carbapenem based antimicrobial compounds. However, these methods do not allow the ester compound to be utilized directly as a substitution reagent; before the said reactions are carried out, the former requires the ester compound to be converted to the corresponding diazonium reagent, while the latter necessitates the conversion of the same to the oxazolidone reagent, respectively.

A method of converting the azetidinone derivative of the general formula (1) directly to the azetidinone derivative of the general formula [3] constitutes a process having one step less as compared with the method of converting the azetidinone derivative of (1) to the sulfone-containing or acyloxy-containing derivative to thereby effect the intended synthesis, and could consequently offer a useful, advantageous synthetic means, only if the method can be brought to practice by a simple and practical operation. If the method permits the reaction to be carried out at lower temperatures and can furthermore allow a readily available reagent to be used in the introduction of a substituent at the 1-methylene group directly without being converted to another reagent, in addition, substantial improvement could be achieved in practical aspects. In view of the above, the present inventors conducted investigation into a method permitting the azetidinone derivatives of the general formula [1] to be converted directly to the azetidinone derivative of the general formula [3] under mild conditions, and have found out the present invention.

SUMMARY OF THE INVENTION

The present inventors found that an ester compound represented by the general formula (2)

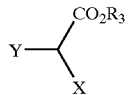
(2)

(wherein $CO_2R_3$, X and Y are as defined above) can be treated with a metal base to give the corresponding metal enolate, which can then be reacted with an azetidinone derivative represented by the general formula (1):

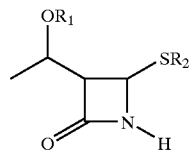
(1)

(wherein $OR_1$ and $R_2$ are as defined above) in the presence of a copper compound to produce a 4-substituted azetidinone derivative represented by the general formula [3]:

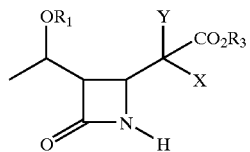
(3)

(wherein $OR_1$, $CO_2R_3$, X and Y are as defined above).

At the same time, it was found that an ester compound represented by the general formula (2):

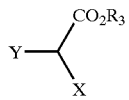
(2)

(wherein $CO_2R_3$, X and Y are as defined above) can be reacted with an azetidinone derivative represented by the general formula (1)

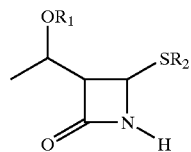
(1)

(wherein $OR_1$ and $R_2$ are as defined above) in the presence of zinc and copper compounds to produce a 4-substituted azetidinone derivative represented by the general formula [3]:

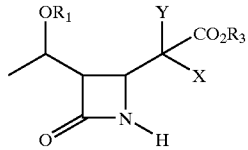
(3)

(wherein $OR_1$, $CO_2R_3$, X and Y are as defined above).

With reference to the decarboxylation reaction of 4-substituted azetidinone derivatives represented by the general formula (4)

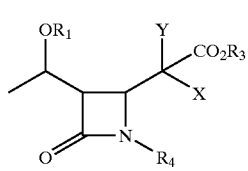
(4)

(wherein $OR_1$, $CO_2R_3$, X and Y are as defined above; $R_4$ is a hydrogen atom or a protective group or a substituent group for amino group), there has been reported a method (Japanese Unexamined Publication No. 5-155850) involving the selection of a type of substituents for $R_4$ to thereby control the configurations of X and Y, and by virtue of the method, highly industrially useful 1-β-substituted derivatives can be produced preferentially. Consequently, the 4-substituted azetidinone derivatives of the general formula (3) as synthesized by the reaction according to the present invention and the 4-substituted azetidinone derivatives of the general formula (4) wherein $R_4$ is a protective group or a substituent group for amino group readily derived from those by conventional methods, and the 4-substituted azetidinone derivatives of the general formula (5)

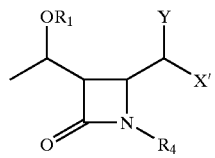
(5)

(wherein $OR_1$, $R_4$ and Y are as defined above; X' is the same as defined for X or a mercapto, hydroxyl, formyl, carboxyl or thiocarboxyl group), which are obtained by converting such derivative to a carboxylic acid compound, followed by decarboxylation, can be utilized as a starting compound for carbapenem compounds of utility as a therapeutic agent for infections.

Such being the case, it was also found that the 4-substituted azetidinone derivatives of the general formulae [3] and [4] are converted to their carboxylic acid compounds for example by way of hydrolysis or a reaction procedure selected from the type of esters, followed by decarboxylation treatment to give the 4-substituted azetidinone derivatives of the general formula (5) useful as a starting material for carbapenem compounds.

The present invention is based on such novel findings and relates to (A) a process for synthesizing 4-substituted azetidinone derivatives of the above-described general formula (3), characterized in that said process comprises reacting an azetidinone derivative of the above-described general formula (1) with an ester compound of the above-described general formula (2) in the presence of zinc and copper compounds, (B) a process for synthesizing 4-substituted azetidinone derivatives of the above-described general formula [3], characterized in that said process comprises treating an ester compound of the above-described general formula (2) with a metal base to give a metal enolate, which is then reacted with an azetidinone derivative of the above-mentioned general formula (1) in the presence of a copper compound, (C) a process for synthesizing 4-substituted azetidinone derivatives of the above-mentioned general formula (5), characterized in that said process comprises converting an ester compound of the above-mentioned general formula (3) and (4) to a carboxylic acid compound, followed by decarboxylated treatment, and (D) novel 4-substituted azetidinone derivatives among the compounds represented by the above-mentioned general formulae (3), (4) and (5) in the above-mentioned processes.

The substitution reaction for the 4-position of the azetidinone derivative of the general formula (1) is normally carried out in hydrocarbon solvents such as benzene and toluene, chlorinated, hydrocarbon solvents such as methylene chloride and chloroform, nitrile, solvents such as acetonitrile, ketone solvents such as acetone and methyl vinyl ketone, ether solvents such as diethyl ether and tetrahydrofuran, and ester solvents such as ethyl acetate, either solely or in mixtures thereof.

The ester compound of the general formula (2) is preferably used in proportions of 1 to 3 equivalents against the azetidinone derivative of the general formula (1). The ester compound is preferably acted on by an equal equivalent of a metal base to produce a metal enolate, followed by addition of the azetidinone derivative of the general formula [1] and a copper compound to allow the reaction. Alternatively, when the ester compound of the general formula (2) is reacted with the azetidinone derivative of the general formula (1) directly without converting to the corresponding metal enolate, the reaction is effected in the above-mentioned solvents, wherein such reaction can be conducted in the presence of zinc and copper compounds by preferably using the ester compound of the general formula [2] in proportions of 1 to 3 equivalents against the azetidinone derivative of the general formula [1].

As the copper compound, there may be mentioned, for example, copper oxides, copper halides, salts of copper with organic carboxylic acids, salts of copper with mineral acids, their complexes and the like. Their preferred examples include cuprous oxide, cupric oxide, cuprous chloride, cupric chloride, cuprous bromide, cupric fluoride, cuprous iodide, cupric perchlorate, cupric nitrate, cupric sulfate, cuprous sulfide, cupric sulfide, cupric trifluoromethanesulfonate, copper cyanide, salts of copper with aliphatic carboxylic acids such as cuprous acetate, cupric acetate, cupric trifluoroacetate, copper propionate and copper butyrate, salts of copper with aromatic carboxylic acids such as copper benzoate, etc., and there are usually employed cuprous halides and their complexes, with cuprous bromide dimethyl sulfide complex being particularly preferred. The used amount each of the copper compounds and zinc is suitably in the range of 1 to 4 equivalents against the azetidinone derivative of the general formula [1]. Meanwhile, preferred examples of the metal base include alkali metal hydride compounds such as sodium hydride and potassium hydride. The reaction temperature varies depending upon the type of the used ester compound of the general formula [2], kind of the azetidinone derivative of the general formula [1], and the like, and is usually in the range of 0° C. to 50° C., suitably in the region of 0° C. to room temperature.

The conversion of the 4-substituted azetidinone derivative of the general formula (3) to the 4-substituted azetidinone derivative of the general formula (4) where $R_4$ is a protective group or a substituent group for the amino group can be done by the conventional procedures.

Referring to the post-reaction treatment, to the reaction solution is added a saturated ammonium chloride solution, followed by extraction of the solution mixture with an organic solvent, and the organic extract layer can be washed with water, dried and concentrated to give the objective compound. The crude reaction product can be used in the subsequent reaction directly without being purified, but can also be purified by recrystallization or column chromatography, if necessary.

The conversion reaction of the ester compound of the general formulae (3) and (4) to the corresponding carboxylic acid compound is usually carried out, in pyridine based solvents such a pyridine, lutidine and collidine, nitrile based solvents such as acetonitrile, ketones based solvents such as acetone and methyl vinyl ketone, ester based solvents such as tetrahydrofuran, and alcohol based solvents such as methanol and ethanol, either solely or in solvent mixtures thereof, suitably in pyridine, collidine or tetrahydrofuran, by hydrolysis in the process of a base, for example, by adding an aqueous solution of a metal hydroxide compound to the compound of general formulae (3) and (4) or under the conditions of a selective procedure adopted according to the type of the ester compound.

The condition of the selective reaction procedure according to the type of the ester compounds can be exemplified by the reaction utilizing metals such as palladium for allyl ester, the catalytic hydrogenation procedures for benzyl ester, the procedures utilizing zinc for trichloroethyl ester, and the like, and these all are known and can be carried out in accordance with the descriptions given in various pieces of literature and the like.

The metal hydroxide compound is preferably used in proportions of 1 to 2 equivalents against the ester compound to conduct the reaction at a temperature in the range of normally 0° C. to 50° C., preferably 0° C. to room temperature. Examples of the metal hydroxide compound include alkali metal hydroxide compounds such as sodium hydroxide, potassium hydroxide and lithium hydroxide, and alkaline earth metal hydroxide compounds such as barium hydroxide.

The decarboxylation reaction of the carboxylic acid compound to form the 4-substituted azetidinone derivative of the general formula (5) can be carried out, for example, by adding an acid in an amount equivalent to the metal hydroxide compound used in the hydrolysis to give the carboxylic acid compound, followed by heating normally at 50° C. to 200° C., preferably 100° C. to 150° C. The acid can be exemplified by mineral acids such as hydrochloric acid, sulfuric acid and nitric acid, organic acids such as acetic acid, propionic acid and camphorsulfonic acid, an aqueous solution thereof, ion exchange resins, etc.

The post-reaction treatment can be effected by concentrating the reaction solution, extracting the concentrate with an organic solvent and washing the organic extract layer with water, followed by drying and concentrating to produce the objective compound. The crude reaction product can be used in the subsequent reaction directly without being purified, but can also be purified by recrystallization or column chromatography, if necessary.

The removal procedure of the protective group for the amino group in $R_4$ of the 4-substituted azetidinone derivative of the general formula (5) varies with the type of the protective group, and can be brought to practice by selecting suitably an appropriate reaction; when the protective group is a tri-substituted silyl group, for example, a weak acid such as dilute hydrochloric acid may be reacted with the azetidinone derivative of (5) while in the case of the protective group being benzyl, phenethyl or benzhydryl group which may be substituted, metallic sodium may be reacted with the derivative of (5) in liquid ammonia by the Barch's reduction.

The 4-substituted azetidinone derivative of the general formula (5) as produced according to the present invention can be utilized, directly or after removal or replacement of the protective group for the amino group in $R_4$, as a starting compound for carbapenem based compounds.

The conversion procedure to a carbapenem based compound varies depending upon the kind of substituents at the 4-position, and can be conducted into practice by a suitably selected reaction, for example, in accordance with the descriptions on the cyclization reaction (Hatanaka, M. et al., Tetrahedron Lett., 1981, 22, 3883) by way of Diechmann reaction, reductive cyclization reaction (Shibata, T. et al., J. Antibiotics, 1989, 42, 374) with use of phosphite, cyclization reaction (Guthikonda, R. N. et al., J. Med. Chem., 1987, 30, 871) based on Wittig reaction, cyclization reaction with use of transitional metals (Ratcliffe, R. W. et al., Tetrahedron Lett., 1980, 21, 1193) and the like.

The protected hydroxyl group represented by $OR_1$ is not particularly limited and comprehends hydroxyl groups protected with protective groups conventionally used for the hydroxyl group, which are exemplified by tri-substituted silyloxy groups, specifically trialkylsilyloxy, aryl(alkyl)alkoxysilyloxy, alkoxydiarylsilyloxy, triarylsilyloxy, alkyldiarylsilyloxy, aryldialkylsilyloxy, and triaralkylsilyloxy groups, etc., such as trimethylsilyloxy, triethylsilyloxy, triisopropylsilyloxy, dimethylhexylsilyloxy, tert-butyldimethylsilyloxy, methyldiisopropylsilyloxy, isopropyldimethylsilyloxy, tert-butylmethoxyphenylsilyloxy, tert-butoxydiphenylsilyloxy, triphenylsilyloxy, tert-butyldiphenylsilyloxy, dimethylcumylsilyloxy and tribenzylsilyloxy groups, etc.; lower alkoxy groups which may have at least one suitable substituent, such as methoxymethoxy, methoxyethoxymethoxy and triphenylmethoxy groups; lower alkanoyloxy groups which may have at least one suitable substituent, such as acetoxy, chloroacetoxy, methoxyacetoxy, propionyloxy, butyryloxy, isobutyryloxy, valeryloxy, pivaloyloxy, hexanoyloxy, 2-ethylbutyryloxy, 3,3-dimethylbutyryloxy and pentanoyloxy groups; lower alkoxycarbonyloxy groups which may have at least one suitable substituent, such as methoxycarbonyloxy, ethoxycarbonyloxy, propoxycarbonyloxy, isopropoxycarbonyloxy, tert-butoxycarbonyloxy, 2-iodoethoxycarbonyloxy, 2,2-dichloroethoxycarbonyloxy and 2,2,2-trichloroethoxycarbonyloxy groups; lower alkenyloxycarbonyloxy groups which may have at least one suitable substituent, such as vinyloxycarbonyloxy, allyloxycarbonyloxy and 2-chloroallyloxycarbonyloxy groups; arylcarbonyloxy groups which may have at least one suitable substituent, such as benzoyloxy group; aralkyloxycarbonyloxy groups which may have at least one suitable substituent, such as benzyloxycarbonyloxy, p-nitrobenzyloxycarbonyloxy, p-methoxybenzyloxycarbonyloxy, phenethyloxycarbonyloxy, trityloxycarbonyloxy, benzhydryloxycarbonyloxy, bis(methoxyphenyl)methyloxycarbonyloxy, 3,4-dimethoxybenzyloxycarbonyloxy and 4-hydroxy-3,5-di-tert-butylbenzyloxycarbonyloxy groups; aryloxycarbonyloxy groups which may have at least one suitable substituent, such as phenyloxycarbonyloxy, 4-chlorophenyloxycarbonyloxy, tolyloxycarbonyloxy, tert-butylphenyloxycarbonyloxy, xylyloxycarbonyloxy, mesityloxycarbonyloxy and cumenyloxycarbonyloxy groups; aralkyloxy groups which may have at least one suitable substituent, such as benzyloxy, p-nitrobenzyloxy, p-methoxybenzyloxy, p-tert-butylbenzyloxy, 3,4-dimethylbenzyloxy, 2,4-dimethoxybenzyloxy, benzhydryloxy and trityloxy groups; heterocyclic-oxy groups which may have at least one suitable substituent, such as tetrahydropyranyloxy group. Unless otherwise specified particularly, the term "lower" designates the same meaning in the below description throughout the present specification, and means preferably 1 to 6 in number of carbon atoms, particularly preferably 1 to 4 in number of carbon atoms.

The group represented by $R_2$ is not particularly limited, but examples of such group, which are readily available and can be produced at low costs, include alkyl groups being exemplified by linear or branched lower alkyl groups such as methyl, ethyl, n-propyl, isopropyl, n-butyl, tert-butyl and hexyl groups and monocyclic or polycyclic alkyl groups such as cyclopentyl, cyclohexyl, menthyl, fenchyl and bornyl groups; alkenyl groups being exemplified by linear or branched lower alkenyl groups such as vinyl, allyl, 1-propenyl, 2-butenyl and 2-methyl-2-propenyl groups; aromatic groups being exemplified by aryl groups having a number of carbon atoms of 6 to 10 such as phenyl, tolyl, xylyl, mesityl and cumenyl groups and aromatic heterocyclic groups such as pyridyl, pyrimidinyl, pyrazinyl and pyridazinyl groups, wherein such alkyl, alkenyl, and aromatic groups individually may be substituted with one or not less than two substituents, for example, halogne atoms such as fluorine, chlorine and bromine atoms; linear or branched lower alkyl groups such as methyl, ethyl, n-propyl, isopropyl, n-butyl, tert-butyl and hexyl groups; monocyclic or poycyclic alkyl groups such as cyclopentyl, cyclohexyl, menthyl, fenchyl and bornyl groups; linear or branched lower alkoxy groups such as methoxy and ethoxy groups; carboxyl group; amino group; nitro group; cyano group; hydroxyl group; aryl groups having a number of carbon atoms of 6 to 10, such as phenyl, tolyl, xylyl, mesityl and cumenyl groups, which may be substituted with the above-mentioned halogen atoms, and lower alkyl, lower alkoxy, carboxyl, amino, nitro, cyano and hydroxyl groups; aralky groups having a number of carbon atoms of 7 to 24, such as benzyl, phenethyl, trityl and benzhydryl groups, which may be substituted with the above-mentioned halogen atoms, and lower alkyl, lower alkoxy, carboxyl, amino, nitro, cyano and hydroxyl groups.

The group represented by $R_3$ is not particularly limited, only if it can eliminate from the esterified carboxyl group represented by $CO_2R_3$ through hydrolysis or under conditions of the selective procedure according to the type of esters, and its preferred examples include those capable of forming the following esters:

Tri-substituted silyl esters such as trialkylsilyl esters, aryl(alkyl)alkoxysilyl esters, alkoxydiarylsilyl esters, triarylsilyl esters, alkyldiarylsilyl esters, aryldialkylsilyl esters, triaralkylsilyl esters (e.g. trimethylsilyl, triethylsilyl, triisopropylsilyl, dimethylhexylsilyl, tert-butyldimethylsilyl, methyldiisopropylsilyl, isopropyldimethylsilyl, tert-butyl-methoxyphenylsilyl, tert-butoxydiphenylsilyl, triphenylsilyl, tert-butyldiphenylsilyl, dimethylcumylsilyl and tribenzylsilyl esters); tri-substituted silyl lower-alkyl esters such as trialkylsilyl lower-alkyl esters, aryl(alkyl)alkoxysilyl lower-alkyl esters, alkoxydiarylsilyl lower-alkyl esters, triarylsilyl lower-alkyl esters, alkyldiarylsilyl lower-alkyl esters, aryldialkylsilyl lower-alkyl esters, and triaralkylsilyl lower-alkyl esters (e.g. the above exemplified compounds in which the tri-substituted silyl groups are substituted with lower alkyl groups (e.g. linear or branched lower alkyl such as methyl, ethyl, n-propyl, isopropyl, n-butyl, tert-butyl; or hexyl) aromatic heterocyclic esters (e.g. pyridyl, pyrimidinyl, pyrazinyl and pyridazinyl esters); lower alkyl esters (e.g. methyl, ethyl, propyl, isopropyl, butyl, isobutyl, tert-butyl, pentyl and hexyl esters), lower alkyl esters which may have at least one suitable substituent, such as lower alkanoyloxy (lower)alkyl esters [e.g. acetoxymethyl, propionyloxymethyl, butyryloxymethyl, valeryloxymethyl, pivaloyloxymethyl, hexanoyloxymethyl, 1-(or 2-)acetoxyethyl, 1-(or 2- or -3)acetoxypropyl, 1-(or 2- or 3- or 4-)acetoxybutyl, 1-(or 2-)propionyloxyethyl, 1-(or 2- or 3-)propionyloxypropyl, 1-(or 2-butyryloxyethyl, 1-(or 2-)isobutyryloxyethyl, 1-(or 2-)pivaloyloxyethyl, 1-(or 2-)hexanoyloxyethyl, isobutyryloxymethyl, 2-ethylbutyryloxymethyl, 3,3-dimethylbutyryloxymethyl and 1-(or 2-)pentanoyloxyethyl esters], lower alkanesulfonyl (lower)alkyl esters (e.g. 2-methylethyl ester), mono (or di or tri)halo(lower)alkyl esters (e.g. 2-iodoethyl, 2,2-dichloroethyl and 2,2,2-trichloroethyl esters), lower alkoxycarbonyloxy(lower)alkyl esters [e.g. methoxycarbonyloxymethyl, ethoxycarbonyloxymethyl, propoxycarbonyloxymethyl, tert-butoxycarbonyloxymethyl, 1- (or 2-)-methoxycarbonyloxyethyl, 1-(or 2-) ethoxycarbonyloxyethyl and 1- (or 2)-isopropoxycarbonyloxyethyl esters], phthalidylidene (lower)alkyl esters, or (5-lower-alkyl-2-oxo-1,3-dioxolene-4-yl)(lower)alkyl esters [e.g. (5-methyl-2-oxo-1,3-dioxolene-4-yl)methyl, (5-ethyl-2-oxo-1,3-dioxolene-4-yl)methyl and (5-propyl-2-oxo-1,3-dioxolene-4-yl) ethyl esters]; lower alkenyl esters (e.g. vinyl and allyl esters); lower alkynyl esters (e.g. ethynyl and propynyl esters); aryl(lower)alkyl esters which may have at least one suitable substituent [e.g. benzyl, 4-methoxybenzyl, 4-nitrobenzyl, phenethyl, trityl, benzhydryl, bis(methoxyphenyl)methyl, 3,4-dimethoxybenzyl and 4-hydroxy-3,5-di-tert-butylbenzyl esters]; aryl esters which may have at least one suitable substituent (e.g. phenyl, 4-chlorophenyl, tolyl, tert-butylphenyl, xylyl, mesityl and cumenyl esters); phthalidyl esters, etc.

Furthermore, these may be substituted at their individual groups with one or more substituents, being exemplified by halogen atoms such as fluorine, chlorine and bromine atoms; linear or branched lower alkyl groups such as methyl, ethyl, n-propyl, isopropyl, n-butyl, tert-butyl and hexyl groups; monocyclic or polycyclic alkyl groups such as cyclopentyl, cyclohexyl, menthyl, fenchyl and bornyl groups; linear or branched lower alkoxy groups such as methoxy and alkoxy groups; carboxyl group; amino group); nitro group; cyano group; hydroxyl group; aryl groups having a number of carbon atoms of 6 to 10 which may be substituted with the above-mentioned halogen atoms and lower alkyl, lower alkoxy, carboxyl, amino, nitro, cyano and hydroxyl groups, etc., such as phenyl, tolyl, xylyl, mesityl and cumenyl; aralkyl groups having a number of carbon atoms of 7 to 24 which may be substituted with the above-mentioned halogen atoms and lower alkyl, lower alkoxy, carbonyl, amino, nitro, cyano and hydroxyl groups, such as benzyl, phenethyl, trityl and benzhydryl groups; and the below-described heterocyclic groups, acyl and ester groups.

Preferred examples of the groups represented by X and Y include the groups which may be added as a synthetic intermediate for carbapenem based antimicrobial compounds, being specifically exemplified by hydrogen atoms and the below-described groups:

Referring to the alkyl, alkenyl, aralkyl, aryl, alkylthio, alkenylthio, aralkylthio, arylthio, alkyloxy, alkenyloxy, aralkyloxy and aryloxy groups, namely, as the alkyl group, there are mentioned linear or branched lower alkyl groups such as methyl, ethyl, n-propyl, isopropyl, n-butyl, tert-butyl and hexyl groups, and monocyclic or polycyclic alkyl groups such as cyclopentyl, cyclohexyl, menthyl, fenchyl and bornyl groups; the alkenyl group includes for example linear or branched lower alkenyl groups such as vinyl, allyl, 1-propenyl, 2-butenyl and 2-methyl-2-propenyl groups; examples of the aralkyl group include aralkyl groups having a number of carbon atoms of 7 to 24 such as benzyl, phenethyl, trityl and benzhydryl groups; and as the aryl group, there may be mentioned aryl groups having a number of carbon atoms of 6 to 10 such as phenyl, tolyl, xylyl, mesityl and cumenyl groups.

As the silyloxy group, there may be mentioned tri-substituted silyloxy groups, and their specific examples include trialkylsilyloxy, aryl(alkyl)alkoxysilyloxy, alkoxydiarylsilyloxy, triarylsilyloxy, alkyldiarylsilyloxy, aryldialkylsilyloxy and triaralkylsilyloxy groups, being exemplified by trimethylsilyloxy, triethylsilyloxy, triisopropylsilyloxy, dimethylhexylsilyloxy, tert-butyl-dimethylsilyloxy, methyldiisopropylsilyloxy, isopropyldimethylsilyloxy, tert-butylmethoxyphenylsilyloxy, tert-butoxydiphenylsilyloxy, triphenylsilyloxy, tert-butyldiphenylsilyloxy, dimethylcumylsilyloxy and tribenzylsilyloxy groups.

These aryl, alkenyl, aralkyl, aryl, alkylthio, alkenylthio, aralkylthio, arylthio, alkyloxy, alkenyloxy, aralkyloxy, aryloxy and silyloxy groups may be substituted in their individual groups with one or more substituents, for example, halogen atoms such as fluorine, chlorine and bromine atoms; carboxyl group; formyl group; nitro group; cyano group; hydroxyl group; amino group; linear or branched lower alkyl groups such as methyl, ethyl, n-propyl, isopropyl, n-butyl, tert-butyl and hexyl groups; monocyclic and polycyclic alkyl groups such as cyclopentyl, cyclohexyl, menthyl, fenchyl and bornyl groups; linear or branched lower alkenyl groups such as vinyl, allyl, 2-chloroallyl, 1-propenyl, 2-butenyl, and 2-methyl-2-propenyl groups; aryl groups having a number of carbon atoms of 6 to 10 such as phenyl, tolyl, xylyl, mesityl and cumenyl groups; aralkyl groups having a number of carbon atoms of 7 to 24 such as benzyl, phenethyl, trityl and benzhydryl groups; alkylthio; alkenylthio, aralkylthio, arylthio, alkyloxy, alkenyloxy, aralkyloxy and aryloxy groups which correspond individually to the above-mentioned alkyl, alkenyl, aralkyl and aryl groups; alkylsulfinyl and alkylsulfonyl groups that correspond individually to the above-mentioned alkyl groups; aralkylsulfinyl and aralkylsulfonyl groups that correspond individually to the above-mentioned aralkyl groups; arylsulfinyl and arylsulfonyl groups that correspond individually to the above-mentioned aryl groups; carbamoyl groups; carbamoyloxy groups; imino-lower-alkyl groups; imino-lower-alkylamino groups; acyloxy groups that correspond individually to the below-described acyl groups; the above-mentioned silyloxy groups; the below-described heterocyclic, heterocyclic-thio, heterocyclic-oxy, acyl, ester, thioester and amide groups.

Furthermore, the above-described substituents individually may be substituted with one or more of substituents such as the above-described substituents: by way of examples, the substituents for the alkyl groups (as is the same with the alkylthio and alkyloxy groups) include halogen atoms, and carboxyl, formyl, nitro, cyano, hydroxyl, amino, alkyl, alkenyl, aryl, aralkyl, alkylthio, alkenylthio, aralkylthio, arylthio, alkyloxy, alkenyloxy, aralkyloxy, aryloxy, alkylsulfinyl, alkylsulfonyl, aralkylsulfinyl, aralkylsulfonyl, arylsulfinyl, arylsulfonyl, carbamoyl, carbamoyloxy, imino, imino-lower-alkylamino, acyloxy, silyloxy, heterocyclic, heterocyclic-thio, heterocyclic-oxy, acyl, ester, thioester and amide groups; as the substituents for the alkenyl groups (as is the same with the alkenylthio and alkenyloxy groups), there may be mentioned halogen atoms, and carboxyl, formyl, nitro, cyano, hydroxyl, amino, alkyl, aryl, aralkyl, alkylthio, alkenylthio, aralkylthio, arylthio, alkyloxy, alkenyloxy, aralkyloxy, aryloxy, alkylsulfinyl, alkylsulfonyl, aralkylsulfinyl, aralkylsulfonyl, arylsulfinyl, arylsulfonyl, carbamoyl, carbamoyloxy, imino-lower-alkyl, imino-lower-alkylamino, acyloxy, silyloxy, heterocyclic, heterocyclic-thio, heterocyclic-oxy, acyl, ester, thioester and amide groups; the substituents for the aralkyl groups (as is the same with the aralkylthio and aralkyloxy groups) include for example halogen atoms, and carboxyl, formyl, nitro, cyano, hydroxyl, amino, alkyl, alkenyl, aryl, aralkyl, alkylthio, alkenylthio, aralkylthio, arylthio, alkyloxy, alkenyloxy, aralkyloxy, aryloxy, alkylsulfinyl, alkylsulfonyl, aralkylsulfinyl, aralkylsulfonyl, arylsulfinyl, arylsulfonyl, carbamoyl, carbamoyloxy, imino-lower-alkyl, imino-lower-alkylamino, acyloxy, silyloxy, heterocyclic, heterocyclic-thio, heterocyclic-oxy, acyl, ester, thioester and amide groups; as the substituents for the aryl groups (as is the same with the arylthio and aryloxy groups), there may be mentioned halogen atoms, and carboxyl, formyl, nitro, cyano, hydroxyl, amino, alkyl, alkenyl, aryl, aralkyl, alkylthio, alkenylthio, aralkylthio, arylthio, alkyloxy, alkenyloxy, aralkyloxy, aryloxy, alkylsulfinyl, alkylsulfonyl, aralkylsulfinyl, aralkylsulfonyl, arylsulfinyl, arylsulfonyl, carbamoyl, carbamoyloxy, imino-lower-alkyl, imino-lower-alkylamino, acyloxy, silyloxy, heterocyclic, heterocyclic-thio, heterocyclic-oxy, acyl, ester, thioester and amide groups; and the substituents for the amino, carbamoyl, carbamoyloxy, imino-lower-alkyl, imino-lower-alkylamino and amide groups include for example halogen atoms, and carboxyl, formyl, nitro, cyano, hydroxyl, amino, alkyl, alkenyl, aryl, aralkyl, alkylthio, alkenylthio, aralkylthio, arylthio, alkyloxy, alkenyloxy, aralkyloxy, aryloxy, alkylsulfinyl, alkylsulfonyl, aralkylsulfinyl, aralkylsulfonyl, arylsulfinyl, arylsulfonyl, carbamoyl, carbamoyloxy, imino-lower-alkyl, imino-lower-alkylamino, acyloxy, silyloxy, heterocyclic, heterocyclic-thio, heterocyclic-oxy, acyl, ester, thioester and amide groups.

The term "heterocyclic group" in the heterocyclic, heterocyclic-thio and heterocyclic-oxy groups is understood to comprehend saturated or unsaturated, monocyclic or polycyclic heterocyclic groups having at least one hetero atom such as oxygen, sulfur and nitrogen atoms, and their preferred examples include 3- to 8-membered, particularly preferably 5- or 6-membered unsaturated monocyclic heterocyclic groups having 1 to 4 nitrogen atoms such as pyrrolyl, pyrrolinyl, imidazolyl, pyrazolyl and pyridyl groups and their N-oxides, pyrimidyl, pyrazinyl, pyridazinyl, triazolyl (e.g. 4H-1,2,4-triazolyl, 1H-1,2,3-triazolyl and 2H-1,2,3-triazolyl groups), tetrazolyl (e.g. 1H-tetrazolyl and 2H-tetrazolyl groups) and dihydrotriazinyl (e.g. 4,5-dihydro-1,2,4-triazinyl and 2,5-dihydro-1,2,4-triazinyl groups) groups; 3- to 8-membered, particularly preferably 5- or 6-membered saturated monocyclic heterocyclic groups having 1 to 4 nitrogen atoms such as azetidinyl, pyrrolidinyl, imidazolidinyl, piperazinyl, pyrazolidinyl and piperazinyl groups; 7- to 12-membered, unsaturated polycyclic heterocyclic groups having 1 to 5 nitrogen atoms such as indolyl, isoindolyl, indolizinyl, benzimidazolyl, quinolyl, isoquinolyl, indazolyl, benzotriazolyl, tetrazopyridyl, tetrazopyridazinyl (e.g. tetrazo[1,5-b]pyridazinyl group) and dihydrotriazolopyridazinyl; 3- to 8-membered, particularly preferably 5- or 6-membered unsaturated monocyclic heterocyclic groups having 1 to 2 oxygen atoms and 1 to 3 nitrogen atoms such as oxazolyl, isoxazolyl and oxadiazolyl (e.g. 1,2,4-oxadiazolyl, 1,3,4-oxadiazolyl and 1,2,5-oxadiazolyl groups) groups; 3- to 8-membered, particularly preferably 5- or 6-membered saturated monocyclic heterocyclic groups having 1 to 2 oxygen atoms and 1 to 3 nitrogen atoms such as morpholinyl group; 7- to 12-membered unsaturated polycyclic heterocyclic groups having 1 to 2 oxygen atoms and 1 to 3 nitrogen atoms such as benzoxazolyl and benzoxadiazolyl groups; 3- to 8-membered, particularly preferably 5- or 6-membered unsaturated monocyclic heterocyclic groups having 1 to 2 sulfur atoms and 1 to 3 nitrogen atoms such as 1,3-thiazolyl, 1,2-thiazolyl, thiazolinyl and thiadiazolyl (e.g. 1,2,4-thiadiazolyl, 1,3,4-thiadiazolyl, 1,2,5-thiadiazolyl and 1,2,3-thiadiazolyl groups); 3- to 8-membered saturated monocyclic heterocyclic groups having 1 to 2 sulfur atoms and 1 to 3 nitrogen atoms such as thiazolidinyl group; 7- to 12-membered unsaturated polycyclic heterocyclic groups having 1 to 2 sulfur atoms and 1 to 3 nitrogen atoms such as benzothiazolyl and benzothiadiazolyl groups; 3- to 8-membered, particularly preferably 5- or 6-membered unsaturated monocyclic heterocyclic groups having 1 to 2 oxygen atoms such as furanyl and pyranyl groups; 3- to 8-membered, particularly preferably 5- or 6-membered saturated monocyclic heterocyclic groups having 1 to 2 oxygen atoms such as tetrahydrofuranyl and tetrahydropyranyl groups; 3- to 8-membered, particularly preferably 5- or 6-membered unsaturated monocyclic heterocyclic groups having a sulfur atom such as thienyl group and S-oxide; and 3- to 8-membered, particularly preferably 5- or 6-membered saturated monocyclic heterocyclic groups having a sulfur atom such as tetrahydrothienyl group and S-oxide.

These heterocyclic groups may be substituted in their individual groups with one or more substituents, for example, halogen atoms such as fluorine, chlorine and bromine atoms; carboxyl group; formyl group; nitro group; cyano group; hydroxyl group; amino group; linear or branched lower alkyl; groups such as methyl, ethyl, n-propyl, isopropyl, n-butyl, tert-butyl and hexyl groups; monocyclic and polycyclic alkyl groups such as cyclopentyl, cyclohexyl, menthyl, fenchyl and bornyl groups; linear or branched lower alkenyl groups such as vinyl, allyl, 2-chloroallyl, 1-propenyl, 2-butenyl, and 2-methyl-2-propenyl groups; aryl groups having a number of carbon atoms of 6 to 10 such as phenyl, tolyl, xylyl, mesityl and cumenyl groups; aralkyl groups having a number of carbon atoms of 7 to 24 such as benzyl, phenethyl, trityl and benzhydryl groups; alkylthio, alkenylthio, aralkylthio, arylthio, alkyloxy, alkenyloxy, aralkyloxy and aryloxy groups which correspond individually to the above-mentioned alkyl, alkenyl, aralkyl and aryl groups; alkylsulfinyl and alkylsulfonyl groups that correspond individually to the above-mentioned alkyl groups; aralkylsulfinyl and aralkylsulfonyl groups that correspond individually to the above-mentioned aralkyl groups; arylsulfinyl and arylsulfonyl groups that correspond individually to the above-mentioned aryl groups; carbamoyl groups; carbamoyloxy groups; imino-lower-alkyl groups; imino-lower-alkylamino groups; acyloxy groups that correspond individually to the below-described acyl groups; the above-mentioned silyloxy, heterocyclic, heterocyclic-thio, heterocyclic-oxy groups; the below-described acyl, ester, thioester and amide groups.

Furthermore, the above-described substituents individually may be substituted with one or more of substituents such as the above-described substituents; by way of examples, the substituents for the alkyl groups (as is the same with the alkylthio and alkyloxy groups) include halogen atoms, and carboxyl, formyl, nitro, cyano, hydroxyl, amino, alkyl, alkenyl, aryl, aralkyl, alkylthio, alkenylthio, aralkylthio, arylthio, alkyloxy, alkenyloxy, aralkyloxy, aryloxy, alkylsulfinyl, alkylsulfonyl, aralkylsulfinyl, aralkylsulfonyl, arylsulfinyl, arylsulfonyl, carbamoyl, carbamoyloxy, imino, imino-lower-alkylamino, acyloxy, silyloxy, heterocyclic, heterocyclic-thio heterocyclic-oxy, acyl, ester, thioester and amide groups; as the substituents for the alkenyl groups (as is the same with the alkenylthio and alkenyloxy groups), there may be mentioned halogen atoms, and carboxyl, formyl, nitro, cyano, hydroxyl, amino, alkyl, aryl, aralkyl, alkylthio, alkenylthio, aralkylthio, arylthio, alkyloxy, alkenyloxy, aralkyloxy, aryloxy, alkylsulfinyl, alkylsulfonyl, aralkylsulfinyl, aralkylsulfonyl, arylsulfinyl, arylsulfonyl, carbamoyl, carbamoyloxy, imino-lower-alkyl, imino-lower-alkylamino, acyloxy, silyloxy, heterocyclic, heterocyclic-thio, heterocyclic-oxy, acyl, ester, thioester and amide groups; the substituents for the aralkyl groups (as is the same with the aralkylthio and aralkyloxy groups) include for example halogen atoms, and carboxyl, formyl, nitro, cyano, hydroxyl, amino, alkyl, alkenyl, aryl, aralkyl, alkylthio, alkenylthio, aralkylthio, arylthio, alkyloxy, alkenyloxy, aralkyloxy, aryloxy, alkylsulfinyl, alkylsulfonyl, aralkylsulfinyl, aralkylsulfonyl, arylsulfinyl, arylsulfonyl, carbamoyl, carbamoyloxy, imino-lower-alkyl, imino-lower-alkylamino, acyloxy, silyloxy, heterocyclic, heterocyclic-thio, heterocyclic-oxy, acyl, ester, thioester and amide groups; as the substituents for the aryl groups (as is the same with the arylthio and aryloxy groups), there may be mentioned halogen atoms, and carboxyl, formyl, nitro, cyano, hydroxyl, amino, alkyl, alkenyl, aryl, aralkyl, alkylthio, alkenylthio, aralkylthio, arylthio, alkyloxy, alkenyloxy, aralkyloxy, aryloxy, alkylsulfinyl, alkylsulfonyl, aralkylsulfinyl, aralkylsulfonyl, arylsulfinyl, arylsulfonyl, carbamoyl, carbamoyloxy, imino-lower-alkyl, imino-lower alkylamino, acyloxy, silyloxy, heterocyclic, heterocyclic-thio, heterocyclic-oxy, acyl, ester, thioester and amide groups; and the substituents for the amino, carbamoyl, carbamoyloxy, imino-lower-alkyl, imino-lower-alkylamino and amide groups include for example halogen atoms, and carboxyl, formyl, nitro, cyano, hydroxyl, amino, alkyl, alkenyl, aryl, aralkyl, alkylthio, alkenylthio, aralkylthio, arylthio, alkyloxy, alkenyloxy, aralkyloxy, aryloxy, alkylsulfinyl, alkylsulfonyl, aralkylsulfinyl, aralkylsulfonyl, arylsulfinyl, arylsulfonyl, carbamoyl, carbamoyloxy, imino-lower-alkyl, imino-lower-alkylamino, acyloxy, silyloxy, heterocyclic, heterocyclic-thio, heterocyclic-oxy, acyl, ester, thioester and amide groups.

More specific examples include:

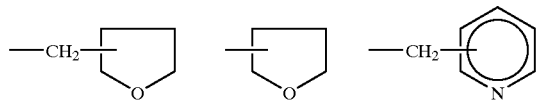

-continued

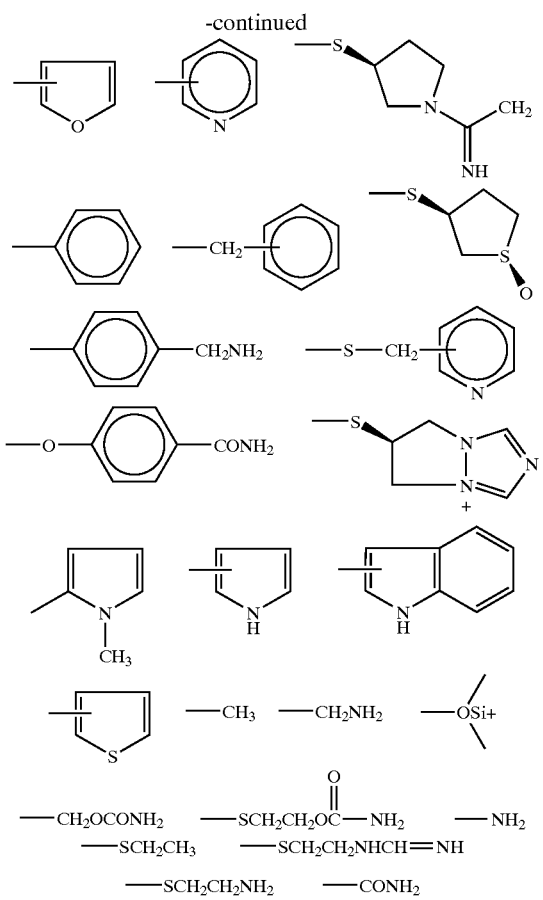

and acyl groups containing them (which have carbonyl group attached to the linkages).

As the acyl group, there may be mentioned alkylcarbonyl, alkenylcarbonyl, aralkylcarbonyl, arylcarbonyl, alkylthiocarbonyl, alkenylthiocarbonyl, aralkylthiocarbonyl, arylthiocarbonyl, alkyloxycarbonyl, alkenyloxycarbonyl, aralkyloxycarbonyl, aryloxycarbonyl, silyloxycarbonyl, heterocyclic-carbonyl, heterocyclic-thiocarbonyl, heterocyclic-oxycarbonyl, estercarbonyl, thioestercarbonyl and amidocarbonyl groups which correspond individually to the above-mentioned alkyl, alkenyl, aralkyl, aryl, alkylthio, alkenylthio, aralkylthio, arylthio, alkyloxy, alkenyloxy, aralkyloxy, aryloxy, silyloxy, heterocyclic, heterocyclic-thio and heterocyclic-oxy groups, as well as the below-described ester, thioester and amide groups.

As the ester and thioester groups, furthermore, there may be mentioned carboxyl and thiocarbonyl groups which are esterified with the above-mentioned alkyl, alkenyl, aralkyl, aryl, alkylthio, alkenylthio, aralkylthio, arylthio, alkyloxy, alkenyloxy, aralkyloxy, aryloxy, silyl, heterocyclic, heterocyclic-thio and heterocyclic-oxy or acyl groups, as well as the below-described amide and amino groups, while examples of the amide and amino groups include amide and amino groups which may be substituted individually for example with one or more of the above-mentioned substituents for the amide and amino groups, etc. As the halogen atom, there may be mentioned fluorine, chlorine and bromine atoms.

Referring to the cycloalkan-2-on-1-yl groups which X and Y are taken together with each other to represent, examples of such cycloalkane include monocyclic ones such as cyclopentane and cyclohexane, which may be substituted individually for example with one or more of the above-mentioned substituents for the alkyl groups.

As the groups represented by X', there may be mentioned the groups represented by X as well as mercapto, hydroxyl, formyl, carboxyl and thiocarboxyl groups.

The groups represented by $R_4$ are not particularly limited, only if they can be adopted as a synthetic intermediate for the carbapenem based antimicrobial compounds, and include for example hydrogen atom or the protective or substituent groups for the amino group to be described in the following:

Namely, preferred examples of the protective and substituent groups for the amino group include alkyl, alkenyl, aralkyl, aryl, acyl, amide and silyl groups and halogen atoms, wherein as the alkyl groups, there may be mentioned linear or branched lower alkyl groups such as methyl, ethyl, n-propyl, isopropyl, n-butyl, tert-butyl and hexyl groups and monocyclic or polycyclic alkyl groups such as cyclopentyl, cyclohexyl, menthyl, fenchyl and bornyl groups; examples of the alkenyl groups include linear or branched lower alkenyl groups such as vinyl, allyl, 1-propenyl, 2-butenyl and 2-methyl-2-propenyl groups; as the aralkyl groups, they may be mentioned, for example, aralkyl groups having a number of carbon atoms of 7 to 24 such as benzyl, phenethyl, trityl and benzhydryl groups; and examples of the aryl groups include aryl groups having a number of carbon atoms of 6 to 10 such as phenyl, tolyl, xylyl, mesityl and cumenyl groups.

As the silyl groups, there may be mentioned tri-substituted silyl groups, which specifically include trialkylsilyl, aryl)alkyl)alkoxysilyl, alkoxydiarylsilyl, triarylsilyl, alkyldiarylsilyl, aryldialkylsilyl and triaralkylsilyl groups, such as trimethylsilyl, triethylsilyl, triisopropylsilyl, dimethylhexylsilyl, tert-butyldimethylsilyl, methyldiisopropylsilyl, isopropyldimethylsilyl, tert-butylmethoxyphenylsilyl, tert-butoxydiphenylsilyl, triphenylsilyl, tert-butyldiphenylsilyl, dimethylcumylsilyl and tribenzylsilyl groups.

These alkyl, alkenyl, aralkyl, aryl and silyl groups may be substituted in their individual groups with one or more of substituents, for example, halogen atoms such as fluorine, chlorine and bromine atoms; carboxyl groups; formyl groups; nitro group; cyano group; hydroxyl group; amino groups; linear or branched lower alkyl groups such as methyl, ethyl n-propyl, isopropyl, n-butyl, tert-butyl and hexyl-groups; monocyclic or polycyclic alkyl groups such as cyclopentyl, cyclohexyl, menthyl, fenchyl and bornyl groups; linear or branched lower alkenyl groups such as vinyl, allyl, 2-chloroallyl, 1-propenyl, 2-butenyl and 2-methyl-2-propenyl groups; aryl groups having a number of carbon atoms of 6 to 10 such as phenyl, tolyl, xylyl, mesityl and cumenyl groups; aralkyl groups having a number of carbon atoms of 7 to 24 such as benzyl, phenethyl, trityl and benzhydryl groups; alkylthio, alkenylthio, aralkylthio, arylthio, alkyloxy, alkenyloxy, aralkyloxy and aryloxy groups which correspond individually to the above-mentioned alkyl, alkenyl, aralkyl and aryl groups; alkylsulfinyl and alkylsulfonyl groups that correspond individually to the above-mentioned alkyl groups; aralkylsulfinyl and aralkylsulfonyl groups that correspond individually to the above-mentioned aralkyl groups; arylsulfinyl and arylsulfonyl groups that correspond individually to the above-mentioned aryl groups; carbamoyl groups; carbamoyloxy groups; imino-lower-alkyl groups; imino-lower-alkylamino groups; acyloxy groups that correspond individually to the below-described acyl groups; the above-mentioned silyloxy groups; the above-described heterocyclic, heterocyclic-thio, heterocyclic-oxy, acyl, ester, thioester and amide groups.

Furthermore, the above-described substituents individually may be substituted with one or more of substituents such as the above-described substituents: by way of examples, the substituents for the alkyl groups (as is the same with the alkylthio and alkyloxy groups) include halogen atoms, and carboxyl, formyl, nitro, cyano, hydroxyl, amino, alkyl, alkenyl, aryl, aralkyl, alkylthio, alkenylthio, aralkylthio, arylthio, alkyloxy, alkenyloxy, aralkyloxy, aryloxy, alkylsulfinyl, alkylsulfonyl, aralkylsulfinyl, aralkylsulfonyl, arylsulfinyl, arylsulfonyl, carbamoyl, carbamoyloxy, imino, imino-lower-alkylamino, acyloxy, silyloxy, heterocyclic, heterocyclic-thio, heterocyclic-oxy, acyl, ester, thioester and amide groups; as the substituents for the alkenyl groups (as is the same with the alkenylthio and alkenyloxy groups), there may be mentioned halogen atoms, and carboxyl, formyl, nitro, cyano, hydroxyl, amino, alkyl, aryl, aralkyl, alkylthio, alkenylthio, aralkylthio, arylthio, alkyloxy, alkenyloxy, aralkyloxy, aryloxy, alkylsulfinyl, alkylsulfonyl, aralkylsulfinyl, aralkylsulfonyl, arylsulfinyl, arylsulfonyl, carbamoyl, carbamoyloxy, imino-lower-alkyl, imino-lower-alkylamino, acyloxy, silyloxy, heterocyclic, heterocyclic-thio, heterocyclic-oxy, acyl, ester, thioester and amide groups; the substituents for the aralkyl groups (as is the same with the aralkylthio and aralkyloxy groups) include for example halogen atoms; and carboxyl, formyl, nitro, cyano, hydroxyl, amino, alkyl, alkenyl, aryl, aralkyl, alkylthio, alkenylthio, aralkylthio, arylthio, alkyloxy, alkenyloxy, aralkyloxy, aryloxy, alkylsulfinyl, alkylsulfonyl, aralkylsulfinyl, aralkylsulfonyl, arylsulfinyl, arylsulfonyl, carbamoyl, carbamoyloxy, imino-lower-alkyl, imino-lower-alkylamino, acyloxy, silyloxy, heterocyclic, heterocyclic-thio, heterocyclic-oxy, acyl, ester, thioester and amide groups; as the substituents for the aryl groups (as is the same with the arylthio and aryloxy groups), there may be mentioned halogen atoms, and carboxyl, formyl, nitro, cyano, hydroxyl, amino, alkyl, alkenyl, aryl, aralkyl, alkylthio, alkenylthio, aralkylthio, arylthio, alkyloxy, alkenyloxy, aralkyloxy, aryloxy, alkylsulfinyl, alkylsulfonyl, aralkylsulfinyl, aralkylsulfonyl, arylsulfinyl, arylsulfonyl, carbamoyl, carbamoyloxy, imino-lower-alkyl, imino-lower-alkylamino, acyloxy, silyloxy, heterocyclic, heterocyclic-thio, heterocyclic-oxy, acyl, ester, thioester and amide groups; and the substituents for the amino, carbamoyl, carbamoyloxy, imino-lower-alkyl, imino-lower-alkylamino and amide groups include for example halogen atoms, and carboxyl, formyl, nitro, cyano, hydroxyl, amino, alkyl, alkenyl, aryl, aralkyl, alkylthio, alkenylthio, aralkylthio, arylthio, alkyloxy, alkenyloxy, aralkyloxy, aryloxy, alkylsulfinyl, alkylsulfonyl, aralkylsulfinyl, aralkylsulfonyl, arylsulfinyl, arylsulfonyl, carbamoyl, carbamoyloxy, imino-lower-alkyl, imino-lower-alkylamino, acyloxy, silyloxy, heterocyclic, heterocyclic-thio, heterocyclic-oxy, acyl, ester, thioester and amide groups.

As the acyl group, there may be mentioned alkylcarbonyl, alkenylcarbonyl, aralkylcarbonyl, arylcarbonyl, alkylthiocarbonyl, alkenylthiocarbonyl, aralkylthiocarbonyl, arylthiocarbonyl, alkyloxycarbonyl, alkenyloxycarbonyl, aralkyloxycarbonyl, aryloxycarbonyl, silyloxycarbonyl, heterocyclic-carbonyl, heterocyclic-thiocarbonyl, heterocyclic-oxycarbonyl, estercarbonyl, thioestercarbonyl and amidocarbonyl groups which correspond individually to the above-mentioned alkyl, alkenyl, aralkyl, aryl, alkylthio, alkenylthio, aralkylthio, arylthio, alkyloxy, alkenyloxy, aralkyloxy, aryloxy, silyloxy, heterocyclic, heterocyclic-thio, heterocyclic-oxy, ester and thioester groups as well as the below-described amide groups.

As the amide groups, furthermore, there may be mentioned amide groups which individually may be substituted with one or more of substituents such as the above-mentioned substituents for the amide groups, and examples of the halogen atoms include fluorine, chlorine and bromine atoms.

The protective groups for the amino group are not particularly limited, and there may be suitably selected and used the conventionally employed protective groups, preferred examples of which are exemplified by the above-mentioned silyl groups; lower-alkoxy lower alkyl groups which may have at least one suitable substituent, such as methoxymethyl and methoxyethoxymethyl groups; aralkyloxycarbonyl-lower-alkyl groups which may have at least one suitable substituent, such as benzyloxycarbonylmethyl, p-nitrobenzyloxycarbonylmethyl, p-methoxybenzyloxycarbonylmethyl, phenethyloxycarbonylmethyl, trityloxycarbonylmethyl, benzhydryloxycarbonylmethyl, bis(methoxyphenyl)methyloxycarbonylmethyl, 3,4-dimethoxybenzyloxycarbonylmethyl and 4-hydroxy-3,5-di-tert-butylbenzyloxycarbonylmethyl groups; aralkyl groups which may have at least one suitable substituent, such as benzyl, p-methoxybenzyl, p-nitro-benzyl, p-tert-butylbenzyl, 3,4-dimethylbenzyl, phenethyl, benzhydryl, trityl, bis(methoxyphenyl)methyl, 2,4-dimethoxybenzyl, 3,4-dimethoxybenzyl, 4-hydroxy-3,5-di-tert-butylbenzyl and 2-naphthylmethyl groups; aralkylcarbonyl groups which may have at least one suitable substituent, such as benzylocarbonyl, p-methoxybenzylcarbonyl, p-nitrobenzylcarbonyl, p-tert-butylbenzylcarbonyl, 3,4-dimethylbenzylcarbonyl, phenethylcarbonyl, benzhydrylcarbonyl, tritylcarbonyl, bis(methoxyphenyl)methylcarbonyl, 2,4-dimethoxybenzylcarbonyl, 3,4-dimethylbenzylcarbonyl, 4-hydroxy-3,5-di-tert-butylbenzylcarbonyl and 2-naphthylmethylcarbonyl groups; heterocyclic groups which may have at least one suitable substituent, such as tetrahydropyranyl group; arylcarbonyl groups which may have at least one suitable substituent, such as benzoyl, chlorobenzoyl, p-methoxybenozyl, p-nitrobenzyl, p-tert-butylbenzoyl, toluoyl and naphthoyl groups; arylcarbonyl-lower-alkyl groups which may have at least one suitable substituent, such as benzoylmethyl, chlorobenzoylmethyl, p-methoxybenzoylmethyl, p-nitrobenzoylmethyl, p-tert-butylbenzoylmethyl, toluoyl-methyl and naphthoylmethyl groups; aryloxy-lower-alkylcarbonyl groups which may have at least one suitable substituent, such as phenoxyacetyl, 4-chlorophenoxyacetyl, tolyloxyacetyl, tert-butylphenoxyacetyl, xylyloxyacetyl, mesityloxyacetyl and cumenyloxyacetyl groups; arylsulfonyl groups which may have at least one suitable substituent, such as benzenesulfonyl, p-tert-butylbenzenesulfonyl and toluenesulfonyl groups; alkylsulfonyl groups which may have at least one suitable substituent, such as mesyl group; formyl group; aliphatic carboxylic acid acyl groups which may have at least one suitable substituent, such as acetyl, chloroacetyl, bromoacetyl, dichloroacetyl, trichloroacetyl, methoxyacetyl, propionyl, butyryl, isobutyryl, valeryl, pivaloyl, hexanoyl, 2-ethylbutyryl, 3,3-dimethyl-butyryl, pentanoyl, caprylyl, decanoyl and acryloyl groups; lower-alkoxycarbonyl groups which may have at least one suitable substituent, such as methoxycarbonyl, ethoxycarbonyl, propoxycarbonyl, isopropoxycarbonyl, tert-butoxycarbonyl, 2-iodoethoxycarbonyl, 2,2-dichloroethoxycarbonyl and 2,2,2-trichloroethoxycarbonyl groups; lower-alkenyloxycarbonyl groups which may have at least one suitable substituent, such as vinyloxycarbonyl, allyloxycarbonyl and 2-chloroallyloxycarbonyl groups; aralkyloxycarbonyl groups which may have at least one suitable substituent, such as benzyloxycarbonyl, p-nitrobenzyloxycarbonyl, benzhydryloxycarbonyl and trityloxycarbonyl groups; aryloxycarbonyl groups which may have at least one suitable substituent, such as phenoxycarbonyl, 4-chlorophenoxycarbonyl and tert-butylphenoxycarbonyl groups; and carbamoyl groups which may have at least one suitable substituent and their corresponding thiocarbamoyl groups; such as methylcarbamoyl, phenylcarbamoyl and naphthylcarbamoyl groups.

EXAMPLES

Below described are examples to illustrate the present invention in more detail, but this invention is not understood to be limited to these examples.

Example 1

Synthesis of (3S,4S)-3-[(R)-1-(tert-butyldimethylsilyloxy)ethyl]-4-di(methoxycarbonyl)methyl-2-azetidinone A solution of dimethyl malonate (291 mg, 2.2 mmole) in tetrahydrofuran (5 ml) was added to a suspension of sodium hydride (90 mg, 2.2 mmole) in tetrahydrofuran (10 ml) in a nitrogen stream, while stirring under ice cooling, and the solution mixture was stirred for 10 min. and then admixed with cuprous bromide dimethylsulfide complex (452 mg, 2.2 mmole), followed by stirring for 15 min, addition of a solution of (3S,4R)-3-[(R)-1-(tert-butyldimethylsilyloxy)ethyl]-4-phenylthio-2-azetidinone (338 mg, 1 mmole) in tetrahydrofuran (10 ml) and stirring for 15 min. The reaction solution was admixed with saturated ammonium chloride solution, and after the insoluble matters were removed by filtration, the filtrate was extracted with ethyl acetate. The ethyl acetate layer was washed with aqueous saturated sodium chloride solution three times, dried over magnesium sulfate and concentrated under reduced pressure, and the residue was purified by silica gel column chromatography (the developing solvent was a 7:1 mixture of n-hexane and ethyl acetate) to give 267 mg (74.4%) of the subject compound in the form of colorless solid.

IR (KBr) cm$^{-1}$: 3158, 3103, 2958, 1770, 1774, 1440, 1202, 836. NMR (CDCl$_3$): δ 0.07(6H,s,—C$\underline{H}_3$)$_2$), 0.88(9H, s,—SiC(C$\underline{H}_3$)$_3$), 1.11(3H,d,J=6.6 Hz, C$\underline{H}_3$CH—OSi), 3.04 (1H,m,C3-H), 3.55(1H,d,J=9.2 Hz, C$\underline{H}$(CO$_2$CH$_3$)$_2$), 3.77 and 3.78(each 3H,s,CO$_2$C$\underline{H}_3$), 4.18–4.28(1H,m,CH$_3$C$\underline{H}$—OSi), 6.06(1H,brs,—N$\underline{H}$)

Example 2

Synthesis of (3S,4S)-3-[(R)-1-(tert-butyldimethylsilyloxy)ethyl]-4-(1,1-di(ethoxycarbonyl)ethyl-2-azetidinone A solution of diethyl 2-methylmalonate (192 mg, 1.1 mmole) in tetrahydrofuran (2.5 ml) was added to a suspension of sodium hydride (44 mg, 1.1 mmole) in tetrahydrofuran (5 ml) in a nitrogen stream, while stirring under ice cooling, and the solution mixture was stirred for 10 min. and then admixed with cuprous bromide dimethylsulfide complex (227 mg, 1.1 mmole), followed by stirring for 15 min, addition of a solution of (3S,4R)-3-[(R)-1-(tert-butyldimethylsilyl)oxy)ethyl]-4-phenylthio-2-azetidinone (169 mg, 0.5 mmole) in tetrahydrofuran (5 ml) and stirring for 15 min. The reaction solution was admixed with saturated ammonium chloride solution, and after the insoluble matters were removed by filtration, the filtrate was extracted with ethyl acetate. The ethyl acetate layer was washed with aqueous saturated sodium chloride solution three times, dried over magnesium sulfate and concentrated under reduced pressure, and the residue was purified by silica gel column chromatography (the developing solvent was a 7:1 mixture of n-hexane and ethyl acetate) to give 106 mg (52.8%) of the subject compound in the form of colorless solid.

IR (KBr) cm$^{-1}$: 3178, 2856, 1769, 1756, 1736, 1256, 1114, 837. NMR (CDCl$_3$): δ 0.07(6H,s,—Si(CH$_3$)$_2$), 0.88 (9H,s,—SiC(CH$_3$)$_3$), 1.14(3H,d,J=5.9 Hz, CH$_3$CH—OSi), 1.23–1.31(6H,m,(CO$_2$CH$_2$CH$_3$)$_2$), 1.46(3H,s,CC H$_3$(CO$_2$CH$_2$CH$_3$)$_2$), 3.01(1H,d,J=1.92 Hz,C4-H), 4.12–4.28 (6H,m,CH$_3$CH—OSi, C3-H and (CO$_2$CH$_2$CH$_3$)$_2$), 5.97(1H, brs,—NH)

Example 3

Synthesis of (3S,4R)-3-[(R)-1-(tert-butyldimethylsilyloxy)ethyl]-4-di(ethoxycarbonyl)fluoromethyl-2-azetidinone A solution of diethyl 2-fluoromalonate (196 mg, 1.1 mmole) in tetrahydrofuran (2.5 ml) was added to a suspension of sodium hydride (44 mg, 1.1 mmole) in tetrahydrofuran (5 ml) in a nitrogen stream, while stirring under ice cooling, and the solution mixture was stirred for 10 min. and then admixed with cuprous bromide dimethylsulfide complex (227 mg, 1.1 mmole), followed by stirring for 15 min, addition of a solution of (3S,4R)-3-[(R)-1-(tert-butyldimethylsilyloxy)ethyl]-4-phenylthio-2-azetidinone (169 mg, 0.5 mmole) in tetrahydrofuran (5 ml) and stirring for 15 min. The reaction solution was admixed with saturated ammonium chloride solution, and after the insoluble matters were removed by filtration, the filtrate was extracted with ethyl acetate. The ethyl acetate layer was washed with aqueous saturated sodium chloride solution three times, dried over magnesium sulfate and concentrated under reduced pressure, and the residue was purified by silica gel column chromatography (the developing solvent was a 7:1 mixture of n-hexane and ethyl acetate) to give 166 mg (82%) of the subject compound in the form of colorless solid.

IR (KBr) cm$^{-1}$, 3169, 3104, 2854, 1744, 1473, 1289, 1251, 836. NMR (CDCl$_3$): δ 0.07(6H,s,—Si(CH$_3$)$_2$), 0.88 (9H,s,—SiC(CH$_3$)$_3$), 1.08(3H,d,J=5.9 Hz, CH$_3$CH—OSi), 1.30–1.36(6H,m,(CO$_2$CH$_2$CH$_3$)$_2$), 3.30(1H,s,C4-H), 4.24–4.45(6H,m,CH$_3$CH—OSi, C3-H and (CO$_2$C H$_2$CH$_3$)$_2$), 5.94(1H,brs,—NH)

Example 4

Synthesis of (3S,4S)-3-[(R)-1-(tert-butyldimethylsilyloxy)ethyl]-4-(hydroxycarbonyl)fluoromethyl-2-azetidinone Dissolved in 1 ml of pyridine was (3S,4S)-3-[(R)-1-(tert-butyldimethylsilyloxy)ethyl]-4-di(ethoxycarbonyl)fluoromethyl-2-azetidinone (405 mg, 1.0 mmole), and 0.5 ml of 4N sodium hydroxide solution was added to the solution, followed by stirring at room temperature for 1.5 hours. The reaction solution was admixed with 0.4 ml of 5N hydrochloric acid and 2.0 ml of 2,4,6-collidine, followed by heating at 150° C. and stirring for 1 hour. After the reaction solution was allowed to cool, the solvent was distilled off, and the residue was dissolved in chloroform. The solution was washed with aqueous saturated potassium hydrogensulfate solution twice, admixed with aqueous saturated sodium hydrogencarbonate solution and separated into two layers. And the aqueous layer was washed with chloroform once, admixed with potassium hydrogensulfate and sodium chloride, and extracted with ethyl acetate. The ethyl acetate layer was washed with aqueous saturated sodium chloride solution twice, dried over magnesium sulfate and concentrated under reduced pressure, and the residue was recrystallized from ethyl acetate/hexane to give 254 mg (83%) of the subject compound consisting of a diasteromer mixture at a ratio of about 2:1 in the form of colorless solid.

IR (KBr) cm$^{-1}$: 3406, 2929, 1748, 1473, 1376, 1254, 1168, 1143, 1112, 1072, 1041, 962, 839, 780. NMR (DMSO-d$_6$) major product: δ 0.02 and 0.05(each 3H,s,—Si(CH$_3$)$_2$), 0.84(9H,s,—SiC(CH$_3$)$_3$), 1.05(3H,d,J=5.9 Hz, C H$_3$CH—OSi), 3.08(1H,m,C3-H), 3.88(1H,m,J=21 Hz,C4-H), 4.13(1H,m,CH$_3$CH—OSi), 5.20(1H,dd,J=49 Hz,2.6 Hz,F—CH—COOH), 8.11(1H,brs,—NH), 13.62(1H,brs,—COOH). By-product: δ 0.03 and 0.05(each 3H,s,—Si(C H$_3$)$_2$), 0.84(9H,s,—SiC(CH$_3$)$_3$), 1.11(3H,d,J=6.6 Hz, C H$_3$CH—OSi), 3.08(1H,m,C3-H), 3.88(1H,m,J=21 Hz,C4-H), 4.13(1H,m,CH$_3$CH—OSi), 5.08(1H,dd,J=48 Hz,4.6 Hz,F—CH—COOH), 8.29(1H,brs,—NH), 13.62(1H,brs,—COOH). MS(FAB) m/z=306(C$_{13}$H$_{24}$NO$_4$FSi+H)$^+$

Example 5

Synthesis of (3S,4S)-3-[(R)-1-(tert-butyldimethylsilyloxy)ethyl]-4-(1-acetyl-1-ethoxycarbonylethyl)-2-azetidinone Ethyl 2-methylacetoacetate (0.87 ml, 6.03 mmole) was added to a suspension of sodium hydride (240 mg, 6.0 mmole) in tetrahydrofuran (5 ml) in a nitrogen stream, and the solution mixture was stirred for 10 min at room temperature and admixed with cuprous bromide dimethylsulfide complex (1.23 g, 5.98 mmole), followed by stirring for 1 hour, addition of (3S,4R)-3-[(R)-1-(tert-butyldimethylsilyloxy)ethyl]-4-phenylthio-2-azetidinone (1.01 g, 2.99 mmole) and stirring for 3 hours. The reaction solution was admixed with saturated ammonium chloride solution, and after the insoluble matters were removed by filtration, the filtrate was extracted with ethyl acetate. The ethyl acetate layer was washed with aqueous saturated sodium chloride solution three times, dried over magnesium sulfate and concentrated under reduced pressure, and the residue was purified by silica gel column chromatography (the developing solvent was a 4:1 mixture of n-hexane and ethyl acetate) to give 876 mg (78.9%) of the subject compound consisting of a diastereomer mixture at a ratio of about 5:4 in the form of colorless solid.

IR (KBr) cm$^{-1}$, 3178, 2957, 2929, 2856, 1767, 1744, 1716, 1646, 1472, 1377, 1362, 1340, 1250, 1159, 1105, 1063, 967, 837, 777. NMR (CDCl$_3$): Major product: δ 0.06(6H,s,—Si(CH$_3$)$_2$), 0.88(9H,s,—SiC(CH$_3$)$_3$), 1.19(3H, d,J=5.9 Hz, CH$_3$CH—OSi), 1.27(3H,t,J=7.2 Hz,CO$_2$CH$_2$C H$_3$), 1.42(3H,s,CCH$_3$(CO$_2$CH$_2$CH$_3$)(COCH$_3$)), 2.21(3H,s, CCH$_3$(CO$_2$CH$_2$CH$_3$)(COCH$_3$)), 2.91(1H,m,C3-H), 4.03 (1H,d,J=2.0 Hz,C4-H), 4.16–4.26(3H,m,CH$_3$CH—OSi and CO$_2$CH$_2$CH$_3$), 5.89(1H,brs,—NH). By-product: δ 0.07(6H, s,—Si(CH$_3$)$_2$), 0.88(9H,s,—SiC(CH$_3$)$_3$), 1.06(3H,d,J=6.6 Hz, CH$_3$CH—OSi), 1.31(3H,t,J=7.2 Hz,CO$_2$CH$_2$CH$_3$), 1.39 (3H,s,CCH$_3$-(CO$_2$CH$_2$CH$_3$)(COCH$_3$)), 2.18(3H,s,CCH$_3$ (CO$_2$CH$_2$CH$_3$)(COCH$_3$)), 2.93(1H,m,C3-H), 4.16–4.26 (4H,m,CH$_3$CH—OSi, C4-H and CO$_2$CH$_2$CH$_3$), 5.89(1H, brs,—NH)

Example 6

Synthesis of (3S,4S)-3-[(R)-1-(tert-butyldimethylsilyloxy)ethyl]-4-(1-acetyl-1-allyloxycarbonylethyl)-2-azetidinone Allyl 2-methylacetoacetate (624 mg, 4.00 mmole) was added to a suspension of sodium hydride (160 mg, 4.0 mmole) in tetrahydrofuran (10 ml) in a nitrogen stream, and the solution mixture was stirred for 10 min at room temperature and then admixed with cuprous bromide dimethylsulfide complex (822 mg, 5.98 mmole), followed by stirring for 1 hour, addition of (3S,4R)-3-[(R)-1-(tert-butyldimethylsilyloxy)ethyl]-4-phenylthio-2-azetidinone (677 mg, 2.00 mmole) and stirring for 3 hours. The reaction solution was admixed with saturated ammonium chloride solution, and after the insoluble matters were removed by filtration, the filtrate was extracted with ethyl acetate. The ethyl acetate layer was washed with aqueous saturated sodium chloride solution three times, dried over magnesium sulfate and concentrated under reduced pressure, and the residue was purified by silica gel column chromatography (the developing solvent was a 3:1 mixture of n-hexane and ethyl acetate) to give 495 mg (64.5%) of the subject compound consisting of a diastereomer mixture (Products A and B) at a ratio of about 1:1 in the form of colorless solid.

IR (KBr) cm$^{-1}$: 3178, 2956, 2929, 2857, 1769, 1715, 1250, 1158, 1104, 1063, 966, 838, 778. NMR (CDCl$_3$): Product A: δ 0.06(6H,s,—Si(CH$_3$)$_2$), 0.88(9H,s,—SiC(CH$_3$)$_3$), 1.19(3H,d,J=6.6 Hz, CH$_3$CH—OSi), 1.44(3H,s,CCH$_3$(CO$_2$)(COCH$_3$)), 2.21(3H,s,CCH$_3$(CO$_2$)(COCH$_3$)), 2.92 (1H,m,C3-H), 4.15–4.24(1H,m,CH$_3$CH—OSi), 4.25(1H,d, J=2.0 Hz,C4-H), 4.62–4.69(2H,m,OCH$_2$CHCH$_2$), 5.28–5.40(2H,m,OCH$_2$CHCH$_2$), 5.83–5.93(2H,m,—NH and OCH$_2$CHCH$_2$). Product B: δ 0.06 (6H,s,—Si(CH$_3$)$_2$), 0.88(9H,s,—SiC(CH$_3$)$_3$), 1.06(3H,d,J=5.9 Hz, CH$_3$CH—OSi), 1.40), 1.40(3H,s,CCH$_3$(CO$_2$)(COCH$_3$), 2.18 (3H,s,CCH$_3$(CO$_2$)(COCH$_3$), 2.94(1H,m,C3-H), 4.05(1H,d, J=2.6 Hz, C4-H), 4.15–4.24(1H,m,CH$_3$CH—OSi) 4.62–4.69(2H,m,OCH$_2$CHCH$_2$), 5.28–5.40(2H,m,OCH$_2$CHCH$_2$), 5.83–5.93(2H,m,—NH and OCH$_2$CHCH$_2$).

Example 7

Synthesis of (3S,4S)-3-[(R)-1-(tert-butyldimethylsilyloxy)ethyl]-4-(1-acetyl-1-benzyloxycarbonylethyl)-2-azetidinone Benzyl 2-methylacetoacetate (825 mg, 4.00 mmole) was added to a suspension of sodium hydride (160 mg, 4.0 mmole) in tetrahydrofuran (10 ml) in a nitrogen stream, and the solution mixture was stirred for 10 min at room temperature and then admixed with cuprous bromide dimethylsulfide complex (822 mg, 5.98 mmole), followed by stirring for 1 hour, addition of (3S,4R)-3-[(R)-1-(tert-butyldimethylsilyloxy)ethyl]-4-phenylthio-2-azetidinone (677 mg, 2.00 mmole) and stirring for 3 hours. The reaction solution was admixed with saturated ammonium chloride solution, and after the insoluble matters were removed by filtration, the filtrate was extracted with ethyl acetate. The ethyl acetate layer was washed with aqueous saturated sodium chloride solution three times, dried over magnesium sulfate and concentrated under reduced pressure, and the residue was purified by silica gel column chromatography (the developing solvent was a 3:1 mixture of n-hexane and ethyl acetate) to give 673 mg (77.6%) of the subject compound consisting of a diastereomer mixture (Products A and B) at a ratio of about 1:1 in the form of colorless oily matter.

IR (neat) cm$^{-1}$: 3259, 2955, 2930, 2856, 1770, 1713, 1498, 1462, 1455, 1373, 1360, 1253, 1142, 1104, 1067, 960, 837, 778, 695. NMR (CDCl$_3$): Product A: δ 0.05(6H,s,—Si(CH$_3$)$_2$), 0.87(9H,s,—SiC(CH$_3$)$_3$), 1.03(3H,d,J=6.6 Hz, CH$_3$CH—OSi), 1.39(3H,s,CCH$_3$(CO$_2$)(COCH$_3$)), 2.04(3H,s, CCH$_3$(CO$_2$)(COCH$_3$)), 2.92(1H,m,C3-H), 4.11–4.22(1H,m, CH$_3$CH—OSi), 4.27(1H,d,J=2.0 Hz,C4-H), 5.10–5.28(2H, m,OCH$_2$-C$_6$H$_5$), 5.83(1H,brs,—NH), 7.30–7.38(5H,m, C$_6$H$_5$). Product B: δ 0.05 and 0.07(each 3H,s,—Si(CH$_3$)$_2$), 0.88(9H,s,—SiC(CH$_3$)$_3$), 1.17(3H,d,J=6.6 Hz, CH$_3$CH—OSi), 1.43(3H,s,CCH$_3$)(CO$_2$)(COCH$_3$)), 2.12(3H, s,CCH$_3$(CO$_2$)(COCH$_3$)), 2.93(1H,m,C3-H), 4.06(1H,d,J= 2.0 Hz,C4-H), 4.11–4.22(1H,m,CH$_3$CH—OSi), 5.10–5.28 (2H,m,OCH$_2$C$_6$H$_5$), 5.83(1H,brs,—NH), 7.30–7.38(5H,m, C$_6$H$_5$)

Example 8

Synthesis of (3S,4S)-3-[(R)-1-(tert-butyldimethylsilyloxy)ethyl]-4-(1-acetylethyl)-2-azetidinone (3S,4S)-3-[(R)-(tert-Butyldimethylsilyloxy)ethyl]-4-(1-acetyl-1-allyloxycarbonylethyl)-2-azetidinone (192 mg, 0.50 mmol) was dissolved in tetrahydrofuran (10 ml) under a nitrogen stream, and dimedone (70 mg, 0.50 mmol) and tetrakis(triphenylphosphine)palladium (58 mg, 0.05 mmol) were added to the resultant solution, followed by stirring under reflux heating for 3 hours. The reaction solution was concentrated under reduced pressure, and the residue was purified by silica gel column chromatography (the developing solvent was a 1:1 mixture of n-hexane and ethyl acetate) to give 108 mg (72.0%) of the subject compound consisting of a diastereomer mixture at a ratio of about 5:1 in the form of colorless solid.

IR (KBr) cm$^{-1}$: 3314, 2954, 1717, 1713, 1654, 1617, 1437, 1308, 1276, 1170, 840. NMR (CDCl$_3$): Major product: δ 0.07 and 0.08(each 3H,s,—Si(CH$_3$)$_2$), 0.88(9H,s,—SiC(CH$_3$)$_3$), 1.23(3H,d,J=7.3 Hz, CHCH$_3$(COCH$_3$)), 1.25 (3H,d,J=6.0 Hz,CH$_3$CH—OSi), 2.20(3H,s,CHCH$_3$(COCH$_3$)), 2.58(1H,dq,J=9.9 Hz and 7.6 Hz,CHCH$_3$(COCH$_3$)), 2.72(1H,dd,J=1.3 Hz and 5.9 Hz, C3-H), 3.67(1H,dd,J=2.0 Hz and 9.9 Hz,C4-H), 4.16(1H,m,CH$_3$CH—OSi), 5.98(1H, brs,—NH).

By-product B: δ 0.07(6H,s,—Si(CH$_3$)$_2$), 0.88(9H,s,—SiC(CH$_3$)$_3$), 1.18(3H,d,J=7.2 Hz,CHCH$_3$)(COCH$_3$)), 1.20(3H,d, J=6.6 Hz, CH$_3$CH—OSi), 2.22(3H,s,CHCH$_3$(COCH$_3$)), 2.81(1H,m,CHCH$_3$(COCH$_3$)), 2.87(1H,dd,J=2.0 Hz and 5.3 Hz,C3-H), 3.89(1H,dd,J=2.0 Hz and 4.6 Hz,C4-H), 4.16 (1H,m,CH$_3$CH—OSi), 5.92(1H,brs,—NH), MS(FAB) m/z= 300(C$_{15}$H$_{29}$NO$_3$Si+H)$^+$ Example 9

Synthesis of (3S,4S)-3-[(R)-1-(tert-butyldimethylsilyloxy)ethyl]-4-ethoxycarbonylmethyl-2-azetidinone A mixture of (3S,4S)-3-[(R)-1-(tert-butyldimethylsilyloxy)ethyl]-4-phenylthio-2-azetidinone (338 mg, 1 mmol), zinc (260 mg, 4 mg atom), cuprous bromide dimethylsulfide complex (411 mg, 2 mmol), ethyl bromoacetate (0.23 ml, 2 mmol) and tetrahydrofuran (4.5 ml) was stirred at room temperature for 31 hours. The reaction mixture was admixed with saturated ammonium chloride solution and extracted with ethyl acetate, and the ethyl acetate layer was washed with aqueous saturated sodium chloride solution three times, dried over magnesium sulfate and concentrated under reduced pressure. The residue was purified by silica gel column chromatography (the developing solvent was a 7:1 mixture of n-hexane and ethyl acetate) to give 90 mg (29%) of the subject compound in the form of colorless solid.

IR (KBr) cm$^{-1}$: 3186, 2954, 1761, 1729, 1472, 1248, 1140. NMR (CDCl$_3$): δ 0.08(6H,s,-Si(CH$_3$)$_2$), 0.88(9H,s—SiC(CH$_3$)$_3$), 1.21(3H,d,J=6.6 Hz, CH$_3$CH—OSi), 2.56(1H, dd,J=9.9 Hz and 16.5 Hz,—C$\underline{H}_2$CO$_2$—), 2.73(1H,dd,J=4.0 Hz and 16.5 Hz,—C$\underline{H}_2$CO$_2$—), 2.82(1H,dd,J=2.0 Hz and 4.6 Hz, C3-H), 3.97(1H,m,C4-H), 4.13–4.24(3H,m,CH$_3$C$\underline{H}$—OSi), 6.15(1H,brs,—N$\underline{H}$)

Example 10

(3S,4S)-3-[(R)-1-(tert-Butyldimethylsilyloxy)ethyl]-4-[1,1-di(allyloxycarbonyl)ethyl]-2-azetidinone A solution of diallyl 2-methylmalonate (396 mg, 2 mmol) in tetrahydrofuran (2 ml) was added dropwise to a suspension of sodium hydride (80 mg, 2 mmol) in tetrahydrofuran (5 ml) under an argon stream at 0° C., and the solution mixture was stirred for 5 min and admixed with cuprous bromide dimethylsulfide complex (411 mg, 2 mmol), followed by stirring for 30 min at the same temperature, addition of a solution of (3R,4S)-3-[(R)-1-(tert-butyldimethylsilyloxy)ethyl]-4-phenylthio-2-azetidinone (338 mg, 1 mmole) in tetrahydrofuran (3 ml) and stirring for 1 hour. The reaction solution was admixed with aqueous saturated ammonium chloride solution and extracted with ethyl acetate. The ethyl acetate layer was dried over magnesium sulfate and concentrated under reduced pressure, and the residue was purified by column chromatography (10 g of silica gel; a 8/1 mixture of n-hexane/ethyl acetate) to give 392 mg (92%) of the subject compound in the form of colorless crystals.

NMR (CDCl$_3$): δ 0.07(6H,s,—Si(C$\underline{H}_3$)$_2$), 0.88(9H,s, SiC(C$\underline{H}_3$)$_3$), 1.13(3H,d,J=6.6 Hz, C$\underline{H}_3$CHOSi), 1.50(3H,s,C$\underline{H}_3$), 3.01–3.04(1H,m,C3-$\underline{H}$), 4.18(1H,d,J=2.6 Hz,C4-H), 4.17–4.25(1H,m,C$\underline{H}$OSi), 4.60–4.68(4H,m,C$\underline{H}_2$CH=CH$_2$), 5.23–5.38(4H,m,CH$_2$CH=C$\underline{H}_2$), 5.77–5.95(2H,m,CH$_2$C$\underline{H}$=CH$_2$), 5.95(1H,brs,—NH)

Example 11

(3S,4S)-3-[(R)-1-(tert-Butyldimethylsilyloxy)ethyl]-4-[(RS)-1-allyloxycarbonyl-cyclohexan-2-on-1-yl]-2-azetidinone A solution of 2-allyloxycarbonylcyclohexanone (1.27 g, 6.98 mmol) in tetrahydrofuran (8 ml) was added dropwise to a suspension of sodium hydride (267 mg, 6.98 mmol) in tetrahydrofuran (30 ml) under an argon stream at 0° C., and the solution mixture was stirred for 10 min and admixed with cuprous bromide dimethylsulfide complex (1.44 g, 6.98 mmol), followed by stirring for 15 min at the same temperature, addition of a solution of (3R,4S)-3-[(R)-1-(tert-butyldimethylsilyloxy)ethyl]-4-phenylthio-2-azetidinone (1.18 g, 3.49 mmol) in tetrahydrofuran (8 ml) and stirring for 40 min. The reaction solution was admixed with aqueous saturated ammonium chloride solution and extracted with ethyl acetate. The ethyl acetate layer was washed with aqueous saturated sodium chloride solution, dried over magnesium sulfate and concentrated under reduced pressure, and the residue was purified by column chromatography (50 g of silica gel; a 4/1 mixture of n-hexane/ethyl acetate) to give 340 mg (24%) of the subject compound having the cyclohexanone ring in the R-configuration in the form of colorless crystals and 920 mg (64%) of the subject compound having the cyclohexanone ring in the S-configuration in the form of colorless oily substance.

R-configuration isomer: IR (KBr) cm$^{-1}$: 1718, 1767. NMR (CDCl$_3$): δ 0.06 and 0.07(total 6H,each s,Si(C$\underline{H}_3$)$_2$), 0.87(9H,s,SiC(C$\underline{H}_3$)$_3$), 1.00(3H,d,J=5.9 Hz,C$\underline{H}_3$CHOSi), 1.51–1.90(4H,m), 2.01–2.12(1H,m), 2.36–2.54(3H,m), 2.95–3.00(1H,m,C3-$\underline{H}$), 4.17–4.28(1H,m,C$\underline{H}$OSi), 4.37(1H, d,J=2.0 Hz, C4-H), 4.57–4.70(2H,m,C$\underline{H}_2$CH=CH$_2$), 5.26–5.42(2H,m,CH$_2$CH=C$\underline{H}_2$), 5.67(1H,brs,—NH), 5.82–5.98(1H,m,CH$_2$C$\underline{H}$=CH$_2$)

S-configuration isomer: IR (neat) cm$^{-1}$: 1711, 1766. NMR (CDCl$_3$): δ 0.06 and 0.07(total 6H,each s,Si(C$\underline{H}_3$)$_2$),0.87(9H,s,SiC(C$\underline{H}_3$)$_3$), 1.20(3H,d,J=6.6 Hz,C$\underline{H}_3$CHOSi), 1.39–1.70(3H,m), 1.75–1.88(1H,m), 2.00–2.11 (1H,m), 2.42–2.52(3H,m), 3.12–3.17(1H,m,C3-$\underline{H}$), 3.88 (1H,d,J=2.0 Hz,C4-$\underline{H}$), 4.10–4.22(1H,m,C$\underline{H}$OS), 4.63–4.68 (2H,m,C$\underline{H}_2$CH=CH$_2$), 5.25–5.37(2H,m,CH$_2$CH=C$\underline{H}_2$), 5.78–5.92(1H,m,CH$_2$C$\underline{H}$=CH$_2$), 5.93(1H,brs,—NH)

Example 12

(3S,4S)-3-[(R)-1-(tert-Butyldimethylsilyloxy)ethyl]-4-[(RS)-1-(hydroxycarbonyl)ethyl]-2-azetidinone Triethylamine (60 μl, 0.430 mmol), formic acid (15 μl, 0.401 mmol), triphenylphosphine (3.8 mg, 0.014 mmol) and palladium acetate (1.6 mg, 0.007 mmol) were added to a solution of the compound (61 mg, 0.143 mmol) as obtained in Example 10 in 1,4-dioxane (1.5 ml), successively, under an argon stream, and the reaction mixture was stirred at 100° C. for one and a half hours. The mixture was cooled and admixed with diethyl ether (7 ml) and 0.5N sodium hydroxide solution (7 ml), followed by stirring, and the aqueous layer was adjusted to pH 3 with 1N hydrochloric acid and extracted with ether (30 ml). The extract layer was dried over sodium sulfate and concentrated under reduced pressure to give 36 mg 83%) of the subject compound as a mixture consisting of the α(R-isomer)/β(S-isomer) at a ratio of 3/1.

NMR (CDCl$_3$): δ 0.07 and 0.09(total 6H,s,Si(C$\underline{H}3$)$_2$), 0.88(9H,s,SiC(C$\underline{H}_3$)$_3$), 1.15–1.31(6H,m,C$\underline{H}_3$CHOSi and C$\underline{H}_2$CHCO$_2$H), 2.55(0.75H,dd,J=7.3 and 9.9 Hz,C$\underline{H}$CO$_2$H), 2.70–2.85(1H,m,C$\underline{H}$CO$_2$H and C3-H), 3.02–3.06(0.25H,m, C3-$\underline{H}$), 3.69(0.75H,dd,J=2.0 Hz and 9.9 Hz,C4-$\underline{H}$), 3.95 (0.25H,dd,J=2.0 Hz and 4.5 Hz,C4-$\underline{H}$), 4.12–4.25(1H,m, CHOSi), 6.45(0.25H,brs,—NH), 6.79(0.75H,brs,NH)

Example 13

(3S,4S)-3-[(R)-1-(tert-Butyldimethylsilyloxy)ethyl]-4-[(RS)-cyclohexan-2-on-1-yl]-2-azetidinone Under an argon stream, a solution of triethylamine (87 μl, 0.625 mmol) and formic acid (19 μl, 0.50 mmol) in tetrahydrofuran (1 ml) was added dropwise to a solution of triphenylphosphine (6.6 mg, 0.025 mmol) and palladium acetate (2.8 mg, 0.0125 mmol) in tetrahydrofuran (1.5 ml), and then a solution of the S-isomer (102 mg, 0.25 mmol) of the compound as obtained in Example 11 in tetrahydrofuran (0.8 ml) was added dropwise to the resultant solution, followed by stirring at room temperature for 1 hour. The reaction mixture was admixed with aqueous saturated ammonium chloride solution (5 ml) and extracted with ethyl acetate (30 ml). The ethyl acetate layer was washed with aqueous saturated sodium chloride solution, dried over magnesium sulfate and concentrated under reduced pressure to give the subject compound as a mixture consisting of the α(R-isomer)/β(S-isomer) at a ratio of 2.5/1. Purification by column chromatography (5 g of silica gel; a 2/1 mixture of hexane/ethyl acetate) yielded 73 mg (90%) of the subject compound as a mixture.

α-Form; IR (KBr) cm$^{-1}$: 1710, 1760. NMR (CDCl$_3$): δ 0.06 and 0.07(total 6H,each s,Si(C$\underline{H}_3$)$_2$), 0.88(9H,s,SiC(CH$\underline{H}_3$)$_3$), 1.22(3H,d,J=5.9 Hz,C$\underline{H}_3$CHOSi), 1.32–1.48(1H,m), 1.61–1.76(2H,m), 1.86–2.00(1H,m), 2.06–2.21(2H,m), 2.23–2.48(3H,m), 2.70(1H,dd,J=2.0 and 5.9 Hz,C3-H), 3.61 (1H,dd,J=2.0 and 9.9 Hz,C4-H), 4.07–4.22(1H,m,CHOSi), 6.09(1H,brs,—NH)

β-Form; IR (KBr) cm$^{-1}$: 1706, 1755. NMR (CDCl$_3$): δ 0.06 and 0.07(total 6H,each s,Si(CH$_3$)$_2$), 0.87(9H,s,SiC(CH$_3$)$_3$), 1.23(3H,d,J=5.9 Hz,CH$_3$CHOSi), 1.54–1.81(3H,m), 1.92–2.20(3H,m), 2.26–2.48(2H,m), 2.51–2.61(1H,m), 2.87 (1H,dd,J=2.0 and 4.7 Hz,C3-H), 4.06–4.12(1H,m,C4-H), 4.12–4.24(1H,m,CHOSi), 5.72(1H,brs,NH)

Example 14

(3S,4S)-3-[(R)-1-(tert-Butyldimethylsilyloxy)ethyl]-4-[1,1-di(allyloxycarbonyl)ethyl]-1-(p-nitrobenzyloxycarbonyl)methyl-2-azetidinone Potassium carbonate (323 mg, 1.61 mmol) was added to a solution of the compound (220 mg, 0.517 mmol) obtained in Example 10 and p-nitrobenzyl 1-iodoacetate (0.592 mmol) in N,N-dimethylformamide (5 ml) under an argon stream, followed by stirring at room temperature for 2 hours. The solution mixture was furthermore stirred at 50° C. for 2 hours, cooled, admixed with water (10 ml) and extracted with diethyl ether (45 ml), and the ether layer was washed with aqueous saturated sodium chloride solution (15 ml), dried over magnesium sulfate and concentrated under reduced pressure. The residue was purified by column chromatography (10 g of silica gel, a 20/1 mixture of hexane/ethyl acetate) to give 148 mg (46%) of the subject compound, with 120 mg (54%) of the starting compound being recovered.

NMR (CDCl$_3$): δ 0.02 and 0.06(total 6H,each s, Si(CH$_3$)$_2$), 0.86(9H,s, SiC(CH$_3$)$_3$), 1.20 (3H,d,J=6.0 Hz,CH$_3$CHOSi), 1.54(3H,s,CH$_3$), 3.05(1H,dd,J=2.0 and 5.9 Hz,C3-H), 3.90(1H,d,J=17.8 Hz,C(H)HCO$_2$PNB), 4.08–4.19(1H,m,CHOSi), 4.29(1H,d,J=17.8 Hz,C(H)HCO$_2$PNB), 4.34(1H,d,J=2.0 Hz,C4-H), 4.53–4.64(4H, m,CO$_2$CH$_2$CH=CH$_2$), 5.20–5.36(6H,m,CH$_2$Ar and CH$_2$CH=CH$_2$), 5.75–5.96(2H,m,CH$_2$CH=CH$_2$), 7.55(2H, d,J=9.2 Hz,Ar), 8.22(2H,d,J=9.2 Hz,Ar)

Example 15

(3S,4S)-3-[(R)-1-(tert-Butyldimethylsilyloxy)ethyl]-4-[(R)-1-allyloxycarbonyl-cyclohexan-2-yl]-1-(p-nitrobenzyloxycarbonyl)methyl-2-azetidinone Potassium carbonate (101 mg, 0.733 mmol) was added to a solution of the compound (R-isomer) (100 mg, 0.244 mmol) obtained in Example 11 and p-nitrobenzyl 1-iodoacetate (0.293 mmol) in N,N-dimethylformamide (4 ml) under an argon stream, followed by stirring at room temperature for 12 hours. The solution mixture was furthermore stirred at 50° C. for 2 hours, cooled, admixed with water (6 ml) and extracted with diethyl ether (30 ml), and the ether layer was washed with aqueous saturated sodium chloride solution (10 ml), dried over sodium sulfate and concentrated under reduced pressure. The residue was purified by column chromatography (10 g of silica gel, a 20/1 mixture of dichloromethane/ethyl acetate) to give 39 mg (27%) of the subject compound, with 48 mg (48%) of the starting compound being recovered.

NMR (CDCl$_3$): δ 0.06 and 0.07(total 6H,each s, Si(CH$_3$)$_2$), 0.87(9H,s, SiC(CH$_3$)$_3$), 0.99(3H,d,m,J=6.5 Hz,CH$_3$CHOSi), 1.52–1.71(2H,m), 1.83–1.95(2H,m), 2.21–2.33 (2H,m), 2.36–2.43(2H,m), 3.08–3.10(1H,m,C3-H),4.09(1H,d,J=8.7 Hz, C(H)HCO$_2$PNB), 4.18(1H,d,J=8.7 Hz,C(H)HCO$_2$PNB), 4.18–4.25(1H,m,CHOSi), 4.52(1H,d, J=2.0 Hz, C4-H), 4.63(2H,ddd,J=4.5, 8.8 and 13.5 Hz,CO$_2$CH$_2$CH=CH$_2$), 5.13(1H,d,J=9.0 Hz,C(H)Ar), 5.28(1H,d,J=9.0 Hz, C(H)Ar), 5.29–5.38(2H,m,CH$_2$CH=CH$_2$), 5.83–5.95(1H,m,CH$_2$CH=CH$_2$), 7.54(2H,d,J=9.2 Hz,Ar), 8.22(2H,d,J=9.2 Hz,Ar)

Example 16

(3S,4S)-3-[(R)-1-(tert-Butyldimethylsilyloxy)ethyl]-4-[(RS)-1-(hydroxycarbonyl)ethyl]-1-(p-nitrobenzyloxycarbonyl)methyl-2-azetidinone Triethylamine (32 μl, 0.233 mmol), formic acid (7.3 μl, 0.194 mmol), triphenylphosphine (2.0 mg, 0.0077 mmol) and palladium acetate (1.6 mg, 0.0038 mmol) were added to a solution of the compound (48 mg, 0.0775 mmol) as obtained in Example 14 in 1,4-dioxane (1.5 ml), successively, under an argon stream, and the reaction mixture was stirred at 100° C. for one hour. The mixture was cooled, admixed with potassium hydrogensulfate (5 ml) and extracted with ethyl acetate (25 ml). The ethyl acetate layer was washed with aqueous saturated sodium chloride solution, dried over sodium sulfate and concentrated under reduced pressure to give 45 mg (quant.) of the subject compound as a mixture consisting of the α(R-isomer)/β(S-isomer) at a ratio of 1/1.7.

NMR (CDCl$_3$): δ 0.02–0.08(6H,m,Si(CH$_3$)$_2$), 0.85 and 0.86(total 9H,each s,SiC(CH$_3$)$_3$), 1.19–1.28(6H,m,CH$_3$CHOSi and CH$_3$CHCO$_2$H), 2.71(0.37H,dd,J=7.1 and 7.4 Hz,CHCO$_2$H), 2.83–2.92(1H,m,CHCO$_2$H and C3-H), 3.05 (0.63H,dd,J=2.0 and 6.0 Hz,C3-H), 3.90–4.32(4H,m,CHOSi,CH$_2$CO$_2$ and C4-H), 5.08–5.33(2H,m,CO$_2$CH$_2$), 7.45–7.70(4H,m,Ar)

Example 17

(3S,4S)-3-[(R)-1-(tert-Butyldimethylsilyloxy)ethyl]-4-[(RS)-1-cyclohexan-2-on-1-yl]-1-(p-nitrobenzyloxycarbonyl)methyl-2-azetidinone Triethylamine (13.6 μl, 0.0972 mmol), formic acid (2.9 μl, 0.078 mmol), triphenylphosphine (1.0 mg, 0.0038 mmol) and palladium acetate (0.4 mg, 0.0019 mmol) were added to a solution of the compound (20 mg, 0.0331 mmol) as obtained in Example 15 in tetrahydrofuran (1 ml), successively, under an argon stream, and the reaction mixture was stirred at room temperature for one and a half hours. The mixture was admixed with aqueous saturated sodium chloride solution and extracted with ethyl acetate. The ethyl acetate layer was dried over sodium sulfate and concentrated under reduced pressure to give the subject compound as a mixture consisting of the α(R-isomer)/β(S-isomer) at a ratio of 1/1.3. Purification of the residue by column chromatography (5 g of silica gel; a 5/1 mixture of hexane/ethyl acetate) yielded 4 mg (23%) of the α-form and 7 mg (41%) of the β-form.

α-Form (R-isomer): NMR (CDCl$_3$): δ 0.03 and 0.06(total 6H,each s,Si(CH$_3$)$_2$), 0.86(9H,s,SiC(CH$_3$)$_3$), 1.22(3H,d,J=5.9 Hz, CH$_3$CHOSi), 1.23–1.44(1H,m), 1.55–1.76(2H,m), 1.80–1.97(1H,m), 2.04–2.18(2H,m), 2.18–2.31(2H,m), 2.61–2.75(1H,m,C4CHC=O), 2.80(1H,dd,J=2.0 and 5.3 Hz,C-3H), 3.88(1H,dd,J=2.0 and 9.9 Hz,C4-H), 4.09(1H,d, J=17.8 Hz, CH(H)CO$_2$PNB), 4.10–4.20(1H,m,CHOSi), 4.23(1H,d,J=17.8 Hz,CH(H)CO$_2$PNB), 5.18(2H,q,J=13.2 Hz,CH$_2$Ar), 7.50(2H,d,J=9.2 Hz,Ar), 8.22(2H,d,J=9.2 Hz,Ar)

β-Form (S-isomer): NMR (CDCl$_3$): δ 0.01 and 0.05(total 6H,each s,Si(CH$_3$)$_2$), 0.84(9H,s,SiC(CH$_3$)$_3$), 1.24(3H,d,J=

5.9 Hz,CH₃CHOSi), 1.56–1.89(3H,m), 1.95–2.21(3H,m), 2.23–2.39(2H,m), 2.56–2.66(1H,m,C4CHC=O), 2.95(1H, dd,J=2.6 and 7.2 Hz,C3-H), 3.90(1H,d,J=17.8 Hz,C(H)HCO₂PNB), 4.18(1H,d,J=17.8 Hz,C(H)HCO₂PNB), 4.09–4.21(1H,m,CHOSi), 4.28–4.31(1H,m,C4-H), 5.26(2H, d,J=9.2 Hz,CH₂Ar), 7.55(2H,d,J=9.2 Hz,Ar), 8.23(2H,d,J= 9.2 Hz,Ar)

INDUSTRIAL APPLICABILITY

As has been described above, the present invention can provide a process of converting the 4-position substituent of the azetidinone derivatives of the general formula (1) in one step to produce the derivatives of the general formula (3), and also can allow the derivatives (3) and (4) to undergo a decarboxylation reaction to give the azetidinone derivatives of the general formula (5), thereby enabling the azetidinone derivatives of the general formula (5) to be synthesized easily in a decreased number of steps as compared with the conventionally known procedures.

What is claimed is:

1. A process for synthesizing a 4-substituted azetidinone derivative representative by the formula [3]:

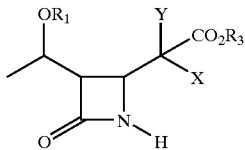

which comprises reacting an azetidinone derivative represented by the formula [1]:

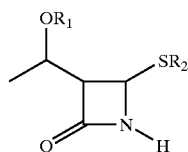

wherein OR₁ is a protected hydroxyl group; R₂ is a substituted or unsubstituted alkyl group, a substituted or unsubstituted alkenyl group or a substituted or unsubstituted aromatic group, in the presence of:

(a) a copper compound selected from the group consisting of copper oxides, copper halides, salts of copper with aliphatic and aromatic carboxylic acids, salts of copper with mineral acids and complexes of cuprous halides, or (b) a mixture of zinc with at least one of said copper compounds with an ester compound represented by the formula [2]:

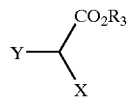

wherein CO₂R₃ is an esterified carboxyl group, selected from the group consisting of, substituted or unsubstituted, tri-substituted silyl carboxyl ester, tri-substituted silyl lower-alkyl carboxyl ester, aromatic heterocyclic carboxylic carboxyl ester, lower alkyl carboxyl ester, lower alkenyl carboxyl ester, lower alkynyl carboxyl ester, aryl lower-alkyl carboxyl ester, aryl carboxyl ester, and phthalidyl carboxyl ester;

wherein X and Y are the same or different and represent individually a substituted or unsubstituted alkyl group, a substituted or unsubstituted alkenyl group, a substituted or unsubstituted aralkyl group, a substituted or unsubstituted aryl group, a substituted or unsubstituted alkylthio group, a substituted or unsubstituted alkenylthio group, a substituted or unsubstituted aralkylthio group, a substituted or unsubstituted arylthio group, a substituted or unsubstituted alkyloxy group, a substituted or unsubstituted alkenyloxy group, a substituted or unsubstituted aralkyloxy group, a substituted or unsubstituted aryloxy group, a substituted or unsubstituted silyloxy group, a substituted or unsubstituted heterocyclic group, a substituted or unsubstituted heterocyclic-thio group, a substituted or unsubstituted heterocyclic-oxy group, a substituted or unsubstituted acyl group, an alkyloxycarbonyl group, an alkenyloxycarbonyl group, an aralkyloxycarbonyl group, an aryloxycarbonyl group, an alkylthiocarbonyl group, an alkenylthiocarbonyl group, an aralkylthiocarbonyl group, an arylthiocarbonyl group, a substituted or unsubstituted aminocarbonyl group, a substituted or unsubstituted amino group, a hydrogen atom or a halogen atom, or, when taken together with the carbon to which they are attached, form a substituted or unsubstituted cycloalkan-2-on-1-yl group;

wherein any substituents on R₂ are selected from the group consisting of halogen, lower alkyl, monocyclic or polycyclic alkyl, lower alkoxy, carboxyl, amino, nitro, cyano, hydroxy, aryl of 6 to 10 carbon atoms and aralkyl groups of 7 to 24 carbon atoms;

wherein any substituents on X and Y are selected from the group consisting of halogen, formyl, nitro, cyano, hydroxyl, amino, lower alkyl, monocyclic and polycyclic alkyl, lower alkenyl, aryl of 6 to 10 carbon atoms, aralkyl of 7 to 24 carbon atoms, alkylthio, alkenylthio, aralkylthio, arylthio, alkyloxy, alkenyloxy, aralkyloxy, aryloxy, alkylsulfinyl, alkylsulfonyl, aralkylsulfinyl, aralkylsulfonyl, arylsulfinyl, arylsulfonyl, carbamoyl, carbamoyloxy, imino-lower-alkyl, imino-lower-alkylamino, acyloxy, silyloxy, heterocyclic, heterocyclic-thio, heterocyclic-oxy, acyl and except when X and Y are acyl, carboxyl, alkyloxycarbonyl, alkenyloxycarbonyl, aralkyloxycarbonyl, aryloxycarbonyl, alkylthiocarbonyl, alkenylthiocarbonyl, aralkylthiocarbonyl, arylthiocarbonyl and a substituted or unsubstituted aminocarbonyl group.

2. The process of claim 1 of synthesizing a 4-substituted azetidinone derivative represented by the formula [3], wherein said process further comprises the steps of treating an ester compound represented by the formula [2] with an alkali metal hydride to convert to the corresponding metal enolate, followed by reaction with an azetidinone derivative represented by the formula [1] in the presence of a copper compound.

3. The process of claim 1 wherein the ester compound represented by the formula [2] is a halogenated acetic acid ester, a malonic acid diester, a 2-alkylmalonic acid diester, a 2-halogenated malonic acid diester, a 2-alkyl-acylacetic acid ester or acycloalkan-2-on-1-carboxylic acid ester.

4. The process of claim 1 wherein the ester compound represented by the formula [2] is a bromoacetic acid ester, a malonic acid diester, 2-methylmalonic acid diester, a 2-fluoromalonic acid diester, a 2-methylacetoacetic acid ester or a cyclohexan-2-on-1-carboxylic acid ester.

5. The process of claim 1 wherein the copper compound is a cuprous bromide dimethylsulfide complex.

* * * * *